United States Patent
Gelbman et al.

(10) Patent No.: US 10,016,167 B2
(45) Date of Patent: Jul. 10, 2018

(54) SYSTEMS, METHODS, AND COMPUTER-READABLE MEDIA FOR TIME LAPSE IMAGE COMPARISON IN GENETIC DISORDER ANALYSIS

(71) Applicant: FDNA Inc., Tortola (VG)

(72) Inventors: Dekel Gelbman, Herzlia Pituach (IL); Yaron Gurovich, Rehovot (IL)

(73) Assignee: FDNA INC., Tortola (VG)

(*) Notice: Subject to any disclaimer, the term of this patent is extended or adjusted under 35 U.S.C. 154(b) by 389 days.

(21) Appl. No.: 14/850,337

(22) Filed: Sep. 10, 2015

(65) Prior Publication Data
US 2015/0374303 A1 Dec. 31, 2015

Related U.S. Application Data

(63) Continuation-in-part of application No. PCT/IB2014/001235, filed on Mar. 12, 2014.
(Continued)

(51) Int. Cl.
*A61B 6/00* (2006.01)
*A61B 5/00* (2006.01)
(Continued)

(52) U.S. Cl.
CPC .......... *A61B 5/7275* (2013.01); *A61B 5/0013* (2013.01); *A61B 5/0022* (2013.01);
(Continued)

(58) Field of Classification Search
CPC ..... A61B 5/7275; A61B 5/746; A61B 5/7282; A61B 5/4538; A61B 5/441; A61B 5/7475; A61B 5/0077; A61B 5/0022; A61B 5/0013; A61B 5/742; A61B 2576/02; A61B 2503/06; A61B 2503/045; A61B 2560/0475; A61B 2576/00; G06K 9/00302; G06K 9/00221; G06K 9/00281; G06K 9/00288; G06T 7/0012; G06T 2207/30201

See application file for complete search history.

(56) References Cited

U.S. PATENT DOCUMENTS

2013/0158437 A1 6/2013 Moalem
2014/0219526 A1 8/2014 Linguraru et al.

FOREIGN PATENT DOCUMENTS

CA 2763503 A1 7/2013

OTHER PUBLICATIONS

Q. Zhao et al., "Automated down syndrome detection using facial photographs," 2013 35th Annual International Conference of the IEEE Engineering in Medicine and Biology Society (EMBC), Osaka, 2013, pp. 3670-3673.*
(Continued)

*Primary Examiner* — Lindsey G Wehrheim
(74) *Attorney, Agent, or Firm* — Finnegan, Henderson, Farabow, Garrett & Dunner LLP

(57) ABSTRACT

Systems, methods, and computer-readable media are disclosed for identifying when a subject is likely to be affected by a medical condition. For example, at least one processor may be configured to receive information reflective of an external soft tissue image of the subject. The processor may also be configured to perform an evaluation of the external soft tissue image information and to generate evaluation result information based, at least in part, on the evaluation. The processor may also be configured to predict a likelihood that the subject is affected by the medical condition based, at least in part, on the evaluation result information.

24 Claims, 29 Drawing Sheets

Related U.S. Application Data

(60) Provisional application No. 61/778,450, filed on Mar. 13, 2013.

(51) Int. Cl.
*G06K 9/00* (2006.01)
*G06T 7/00* (2017.01)

(52) U.S. Cl.
CPC ............ *A61B 5/0077* (2013.01); *A61B 5/441* (2013.01); *A61B 5/4538* (2013.01); *A61B 5/7282* (2013.01); *A61B 5/742* (2013.01); *A61B 5/746* (2013.01); *A61B 5/7475* (2013.01); *G06K 9/00221* (2013.01); *G06K 9/00281* (2013.01); *G06K 9/00288* (2013.01); *G06K 9/00302* (2013.01); *G06T 7/0012* (2013.01); *A61B 2503/045* (2013.01); *A61B 2503/06* (2013.01); *A61B 2560/0475* (2013.01); *A61B 2576/00* (2013.01); *A61B 2576/02* (2013.01); *G06T 2207/30201* (2013.01)

(56) References Cited

OTHER PUBLICATIONS

Hartmut S. Loos et al., "Computer-Based Recognition of Dysmorphic Faces," European Journal of Human Genetics, vol. 11, No. 8, Aug. 2003, pp. 555-560.

Stefan Boehringer et al., "Syndrome Identification Based on 2D Analysis Software," European Journal of Human Genetics, vol. 14, No. 10, Jun. 14, 2006, pp. 1082-1089.

Qian Zhao et al., "Down Syndrome Detection From Facial Photographs Using Machine Learning Techniques," Proceedings of SPIE, vol. 8670, Feb. 26, 2013, pp. 867003-1-867003-7.

EPO Communication in corresponding EP Application No. 14742353.7, dated Oct. 14, 2016, 7 pages.

"Elements of Morphology: Introduction," 2009, Am J Med Genet Part A 149A:2-5, to Allanson et al.

"Elements of Morphology: Standard of terminology for the head and face," 2009, Am J Med Genet Part A 149A:6-28, to Allanson et al.

"Elements of Morphology: Standard terminology for the lips, mouth, and oral region," 2009, Am J Med Genet Part A 149A:77-92, to Carey et al.

"Elements of Morphology: Standard terminology for the periorbital region," 2009, Am J Med Genet Part A 149A:29-39, to Hall et al.

"Elements of Morphology: Standard terminology for the nose and philtrum," 2009, Am J Med Genet Part A 149A:61-76, to Hennekam et al.

"Elements of Morphology: Standard terminology for the ear," 2009, Am J Med Genet Part A 149A:40-60, to Hunter et al.

"Elements of Morphology: Standard terminology for the hands and feet," 2009, Am J Med Genet Part A 149A:93-127, to Biesecker et al.

\* cited by examiner

SYSTEMS, METHODS, AND COMPUTER-READABLE MEDIA FOR TIME LAPSE IMAGE COMPARISON IN GENETIC DISORDER ANALYSIS

RELATED APPLICATIONS

This application is a continuation-in-part of International Application No. PCT/IB2014/001235, filed Mar. 12, 2014, which claims priority to U.S. Provisional Application No. 61/778,450, filed Mar. 13, 2013, both of which are incorporated herein by reference in their entirety.

TECHNICAL FIELD

The present disclosure relates to the field of image analysis. For example, systems, methods, and computer-readable media are disclosed for identifying when a subject is likely to be affected by a medical condition using image analysis.

BACKGROUND

There are thousands of known rare diseases that collectively affect more than 8% of the world's population. Rare diseases are often chronic, progressive, degenerative, and life threatening. Children affected by rare diseases often suffer from many associated medical complications and need critical and timely medical intervention.

Many rare diseases are genetic in origin, inborn, and exhibit symptomatic malformations. Symptomatic malformations are often the first sign of a rare disease. A dysmorphic evaluation performed by a qualified specialist often plays a key factor in recognizing a disease. But due to the rarity of many diseases, the scarcity of dysmorphology experts, and the complexity of a clinical diagnosis, is it often not possible to provide proper and comprehensive dysmorphology training to a large number of physicians. The diagnosis of rare diseases is often very difficult, particularly for physicians that lack the relevant awareness, knowledge, and experience. Most children that do reach a diagnosis are typically diagnosed later in life when physical symptoms, developmental delay, intellectual disability, and other medical complications are observed by their families or treating physician. This can result in an unmanaged and untreated disease that can cause a child's condition to deteriorate.

Early identification of diseases is often critical. Accordingly, systems and methods are needed that can efficiently and noninvasively determine whether a person is likely to be affected by a medical condition.

SUMMARY

Embodiments consistent with the present disclosure provide systems, methods, and computer-readable media for identifying when a subject is likely to be affected by a medical condition using image analysis.

In one disclosed embodiment, a system for identifying when a subject is likely to be affected by a medical condition is disclosed. The system includes at least one processor that is configured to receive information reflective of an external soft tissue image of the subject, perform a first evaluation of the external soft tissue image information using at least one of an anchored cells analysis, a shifting patches analysis and a relative measurements analysis, generate first evaluation result information based, at least in part, on the first evaluation, perform a second evaluation of the external soft tissue image information using at least one of the anchored cells analysis, the shifting patches analysis, and the relative measurements analysis, generate second evaluation result information based, at least in part, on the second evaluation, and predict a likelihood that the subject is affected by the medical condition based, at least in part, on the first evaluation result information and the second evaluation result information.

In another disclosed embodiment, a system for identifying when a subject is likely to be affected by a medical condition is disclosed. The system includes at least one processor that is configured to receive information reflective of an external soft tissue image of the subject, divide the external soft tissue image information into a plurality of regions, generate an analysis of each of the plurality of regions, aggregate the analyses of the plurality of regions, and determine a likelihood that the subject is affected by the medical condition based on the aggregated analyses.

In another disclosed embodiment, a system for identifying when a subject is likely to be affected by a medical condition is disclosed. The system includes at least one processor that is configured to receive information reflective of an external soft tissue image of the subject, use image information analysis to compare the external soft tissue image information with a plurality of external soft tissue images of other subjects in a database, determine, based on the image information analysis, dysmorphic features included in the external soft tissue image information, access descriptors associated with the dysmorphic features, and output at least some of the descriptors.

In another disclosed embodiment, a system for identifying when a subject is likely to be affected by a medical condition is disclosed. The system includes at least one processor that is configured to receive information reflective of an external soft tissue image of the subject, analyze the external soft tissue image information, identify one or more external soft tissue attributes in the external soft tissue image information based, at least in part, on the analysis, access at least one database of external soft tissue attributes associated with a plurality of medical conditions, compare the one or more identified external soft tissue attributes with the external soft tissue attributes of the at least one database, and output information about at least one medical condition likely possessed by the subject based on the comparison.

In another disclosed embodiment, a system for identifying when a subject is likely to be affected by a medical condition is disclosed. The system includes at least one processor that is configured to receive first information reflective of a first external soft tissue image of the subject recorded at a first time, analyze the first image information, receive second information reflective of a second external soft tissue image of the subject recorded at a second time, analyze the second image information, compare the analysis of the first image information with the analysis of the second image information, and predict a likelihood that the subject is affected by the medical condition based, at least in part, on the comparison.

Additional aspects related to the disclosed embodiments will be set forth in part in the description which follows, and in part will be understood from the description, or may be learned by practice of the disclosed embodiments.

It is to be understood that both the foregoing general description and the following detailed description are exemplary and explanatory only and are not restrictive of the claims.

BRIEF DESCRIPTION OF THE DRAWINGS

The accompanying drawings, which are incorporated in and constitute a part of this disclosure, illustrate various disclosed embodiments. In the drawings.

DETAILED DESCRIPTION

Reference will now be made in detail to the example embodiments, which are illustrated in the accompanying drawings. Wherever possible, the same reference numbers will be used throughout the drawings to refer to the same or like parts.

Figure 1:
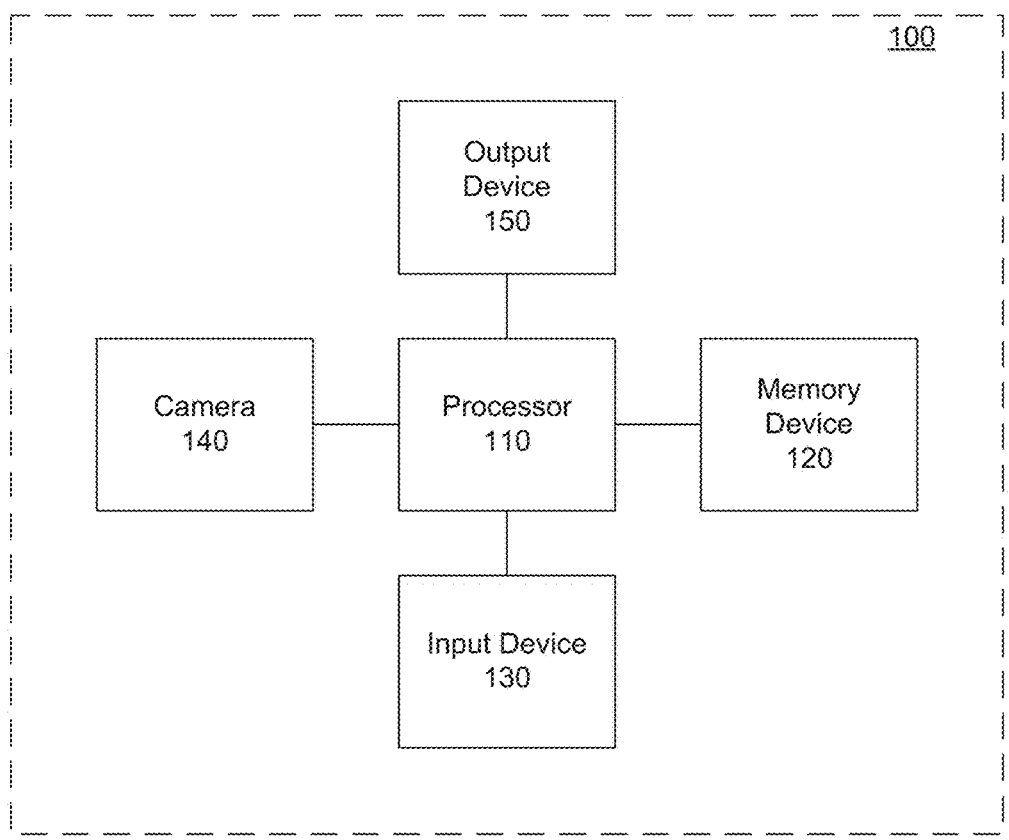
FIG. 1 illustrates an example system for identifying when a subject is likely to be affected by a medical condition that may be used for implementing the disclosed embodiments.

FIG. 1 is a diagram illustrating an example system 100 for identifying when a subject is likely to be affected by a medical condition, consistent with the disclosed embodiments. A subject may include, among other things, any person or type of person, such as a male or female person and a child or adult. A child may include, for example, a neonate, an infant, a toddler, a preschooler, a school age child, or an adolescent. For example, a male or female person from birth to 1 month old may be referred to as a neonate, from 1 month to 1 year old may be referred to as an infant, from 1 year to 3 years old may be referred to as a toddler, from 3 years to 6 years old may be referred to as a preschooler, from 6 years to 12 years old may be referred to as a school age child, and from 12 years to 18 years old may be referred to as an adolescent. An adult may include, for example, a male or female person from 18 years old and onwards. These age ranges, however, are exemplary only. For example, a 19 year old person may be referred to as an adolescent in certain contexts.

A medical condition may include, among other things, any medical disease. A subject possessing a medical condition may include, for example, at least one of possessing a genetic syndrome and being a carrier of a genetic syndrome. A medical condition may also include, among other things, any association of clinically recognizable features, signs, symptoms, phenomena, or other characteristics that often occur together, such that the presence of one feature, sign, symptom, phenomena, or other characteristic may imply, indicate, or alert to the possible presence of the others. A medical condition may also include one or more abnormal findings in physical growth and development over time (e.g., growth deficiencies and craniofacial deformations that develop over time). For example, a medical condition may be one or more of the medical conditions disclosed in "Gorlin's syndromes of the head and neck," 2010, Oxford University Press, to R. C. M. Hennekam et al, "The Bedside Dysmorphologist," 2008, Oxford University Press, to William Reardon, and "Smith's Recognizable Patterns of Human Malformation," 2005, WB Saunders, to Kenneth Lyons Jones, all of which are incorporated herein by reference in their entirety.

In some embodiments, a medical condition includes one or more conditions that may cause a person to exhibit one or more dysmorphic features. A dysmorphic feature may include, for example, any feature that affects the appearance of a subject. A dysmorphic feature may, for example, reflect an external soft tissue dysmorphology. For example, a medical condition may cause a child's skull to form in an irregular manner, which may cause the child's facial appearance to also be irregular in a manner that may be described by one or more dysmorphic features. For example, a dysmorphic feature may be one or more of the dysmorphic features disclosed in "Elements of morphology: Introduction," 2009, Am J Med Genet Part A 149A:2-5, to Allanson et al., "Elements morphology: Standard of terminology for the head and face," 2009, Am J Med Genet Part A 149A: 6-28, to Allanson et al., "Elements of morphology: Standard terminology for the lips, mouth, and oral region," 2009, Am J Med Genet Part A 149A:77-92, to Carey et al., "Elements of morphology: Standard Terminology for the periorbital region," 2009, Am J Med Genet Part A 149A:29-39, to Hall et al., "Elements of morphology: Standard terminology for the Nose and philtrum," 2009, Am J Med Genet Part A 149A:61-76, to Hennekam et al., "Elements of morphology: Standard terminology for the ear," 2009, Am J Med Genet Part A 149A:40-60, to Hunter et al., and "Elements of morphology: Standard terminology for the hands and feet," 2009, Am J Med Genet Part A 149A:93-127, to Biesecker et al., all of which are incorporated herein by reference in their entirety.

Further, when the medical condition is a genetic disorder, predicting the likelihood that the subject is affected by the genetic disorder, as used herein, may include, among other things, the ability to screen for a genetic disorder, reach a definitive or differential diagnosis, rule out a diagnosis, monitor the progression of a genetic disorder, describe the natural history of a genetic disorder, define and evaluate the phenotype associated with a genetic disorder, correlate phenotypic attributes to genetic variants, discover biomarkers for a genetic disorder, facilitate development of new therapies or repurpose existing therapies and test their efficacy, recruit and match candidates for clinical trials, facilitate development of new diagnostic tools and methods, and facilitate development of new or improved bioinformatics solutions. Genetic disorders may include, among other things, a medical condition caused by one or more abnormalities or variants in the genome, including a condition that is present from birth (congenital). Genetic disorders may or may not be heritable. In non-heritable genetic disorders, defects may be caused by new mutations or changes to the DNA.

System 100 may include, among other things, at least one processor 110, at least one memory device 120, at least one input device 130, at least one camera 140, and at least one output device 150. Processor 110 may include any electrical circuit (e.g., processing circuitry) that may be configured to perform an operation on at least one input variable, including, for example one or more integrated circuits, microchips, microcontrollers, and microprocessors, which may be all or part of a central processing unit (CPU), a digital signal processor (DSP), a field programmable gate array (FPGA), a graphical processing unit (GPU), or any other circuit known to those skilled in the art that may be suitable for executing instructions or performing logic operations. As such, the processor 110 may be referred to as processing circuitry in some embodiments.

Multiple functions may be accomplished using a single processor or multiple related and/or unrelated functions may be divided among multiple processors. Processor 110 may be configured to access memory device 120, which may include, for example, persistent memory, ROM, EEPROM, EAROM, flash memory devices, magnetic disks, magneto optical disks, CD-ROM, DVD-ROM, Blu-ray, and the like. Memory device 120 may contain instructions (i.e., software or firmware) or other data, which the processor 110 may be configured to execute. As such, some embodiments of the methods presented herein may be stored on one or more memory devices 120 as computer-executable instructions that may be executed by the processor 110 or any other electrical computer or circuitry. Processor 110 may receive instructions and data stored memory device 120. Thus, in some embodiments, processor 110 may execute the software or firmware to perform functions by operating on input data and generating output. However, processor 110 may also receive or access data stored remotely over a network (not depicted in FIG. 1). For example, device 100 may include a communication device (not depicted in FIG. 1) that enables processor 110 to receive or access data stored remotely on a server or user device over a network. Moreover, processor 110 may also be, for example, dedicated hardware or an application specific integrated circuit (ASIC) that performs processes by operating on input data and generating output. Processor 110 may be any combination of dedicated hardware, one or more ASICs, one or more general purpose processors, one or more DSPs, one or more GPUs, or one or more other processors capable of processing digital information. For example, in some embodiments, processor 110 may comprise multiple processors that may provide parallel processing capabilities.

Figure 2:
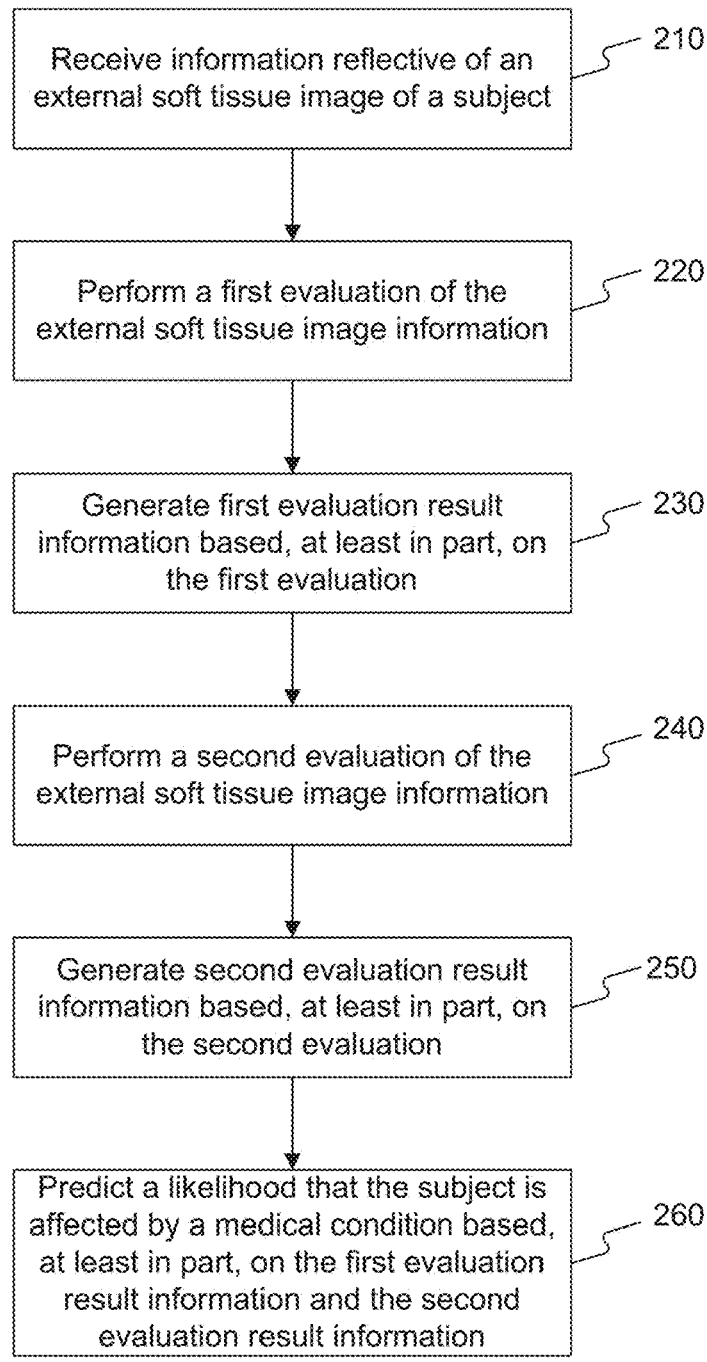
FIG. 2 illustrates example operations that a processor of a medical condition analysis system may be configured to perform to predict a likelihood that a subject is affected by a medical condition using two evaluations, in accordance with some of the disclosed embodiments.

FIG. 2 illustrates an exemplary process 200 that at least one processor may be configured to perform. For example, as discussed above, processor 110 may be configured to perform process 200 by executing software or firmware stored in memory device 120, or may be configured to perform process 200 using dedicated hardware or one or more ASICs.

Processor 110 may be configured to receive information reflective of an external soft tissue image of the subject (step 210). For example, processor 110 may receive information, such as pixel values, reflective of an external soft tissue image of a subject captured by camera 140. Camera 140 may include, among other things, one or more image sensors, such as a CCD image sensor, a CMOS image sensor, a camera, a light sensor, an IR sensor, an ultrasonic sensor, a proximity sensor, a shortwave infrared (SWIR) image sensor, a reflectivity sensor, or any other image sensor that is capable of capturing an external soft tissue image. An image sensor may be configured to capture any quantity of image data, such as single pixel data, one-dimensional line data, two-dimensional data, or three-dimensional data. Camera 140 may be a fixed camera, mobile camera, or any other image capturing device or equipment, which may, for example, be further incorporated into a computer, a tablet, a phone, glasses, or any other device.

An external soft tissue image may include, among other things, an image, such as a digital image comprised of pixels, of a subject or any portion of a subject. In some embodiments, the external soft tissue image may include an image of at least one of a face of the subject, a cranium of the subject, a hand of the subject, and a foot of the subject. In such embodiments, the external soft tissue image may be referred to as a type of external image of the subject, for example, an external cranio-facial soft tissue image, which may be an external soft tissue image of the cranio-facial portion of the subject. However, the external soft tissue image may also include other portions of the subject, such as, such as a hairline, forehead, ocular region, eyebrow, nose, eye, mid-face region, philtrum region, mouth, ear, mandibular region, chin, cheek, neck, chest, mid-body, back, torso, hips, genitalia, limbs, joints, hands, and fingers. In some embodiments, the external soft tissue image is a cranio-facial image that includes at least one of a frontal view, a lateral view, an angled view, a top view, and a back view. As used herein, a cranio-facial image is an image that includes at least a portion of a cranium or face of the subject. A frontal view may include an image of the front of the face of the subject. A lateral view may include an image taken at or approximately at a 20-90 degree angle (to the left and/or right side of the face) from the vertical midline of the head of the subject. For example, in one embodiment, the lateral view may include an image taken at or approximately at a 45 degree angle (to the left and/or right side of the face) from the vertical midline of the head of the subject. A top view may include an image of the top of the head of the subject. A back view may include an image of the back of the head of the subject. As described in more detail below, in some embodiments the external soft tissue image is associated with a dysmorphology.

The information reflective of an external soft tissue image received by processor 110 may include the external soft tissue image itself or any data derived from the external soft tissue image (e.g., a separate processor at camera 140 may derive data from the external soft tissue image and transmit the derived data to processor 110). For example, if the external soft tissue image is an analog image (although the external soft tissue image may be captured as a digital image), information reflective of an external soft tissue image may include a digitally converted version of the external soft tissue image. The information reflective of an external soft tissue image may be, for example, a vector image or a raster image. The information reflective of an external soft tissue image may also be non-image data, such as a set of parameters derived from the external soft tissue image, which may include, for example, one or more intensities of the image, one or more locations of edges in the image, and one or more textures in the image.

Figure 18:
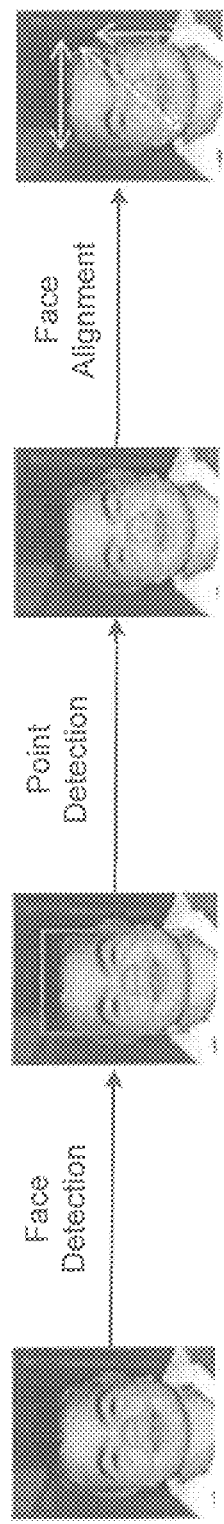
FIG. 18 illustrates exemplary depictions of an image processing pipeline in accordance with some of the disclosed embodiments.

In some embodiments, processor 110 may preprocess the external soft tissue image information as it receives the information and/or after it receives the information. FIG. 18 depicts one example of a preprocessing routine that may be performed by processor 110. As depicted in FIG. 18, as part of a preprocessing routine, processor 110 may be configured to detect a face region of the external soft tissue image information, detect a number of points in the face region, and align the face region. One example of a face detection routine is shown in FIGS. 19-22. For example, as graphically depicted in FIG. 20, processor 110 may be configured to detect a face region by first placing a plurality of patches (i.e., sub-regions of the image information), which optionally may overlap one another, over the image information. For each patch, a descriptor vector may be computed. A descriptor vector may include, for example, data derived from at least one of a scale-invariant feature transform (SIFT), a histogram of oriented gradients (HOG), a self-similarity descriptor, a histogram of Local Binary Patterns, a descriptor based on the activation of at least one layer in a neural network, and any other determinable feature known in the image analysis and computer vision fields.

Figure 19:
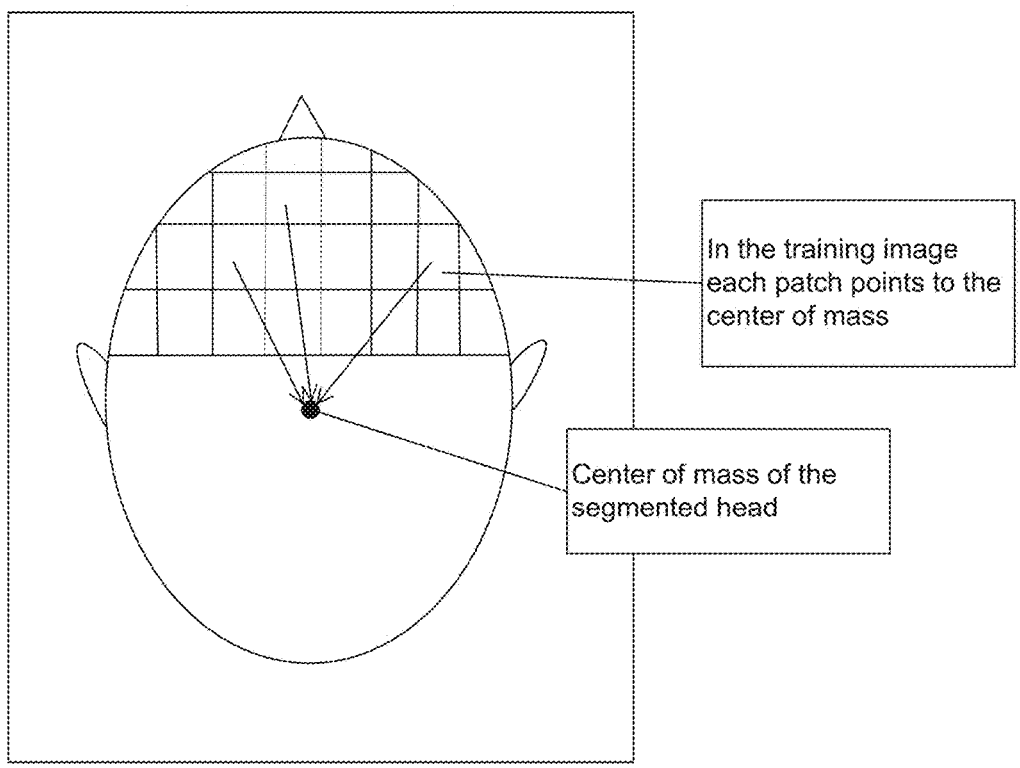
FIGS. 19-22 illustrate exemplary depictions of image segmentation in accordance with some of the disclosed embodiments.

During a training phase for the face detection routine, one or more regions of a set of training images may be manually outlined. For example, processor 110 may determine an outline of a head and one or more regions within a face or side of a face (e.g., an outline of eyes, nose, mouth, ears, etc.). Processor 110 may determine a center of mass of the outline of the head (e.g., a point where the weighted relative position of the points on the outline sums to zero). Processor 110 may further determine a descriptor vector for each patch of each training image and store the descriptor vectors in a database. The database may be stored by memory device 120, or may be stored on, for example, a remote server that is accessible to processor 110 over a network. Moreover, information regarding the location of the center of mass of the head shape relative to the center of each patch associated with a descriptor vector may also be stored in the database. FIG. 19 depicts an example of an outlined head shape with information regarding the location of the center of mass of the head shape relative to the center of a plurality of patches.

Figure 20:
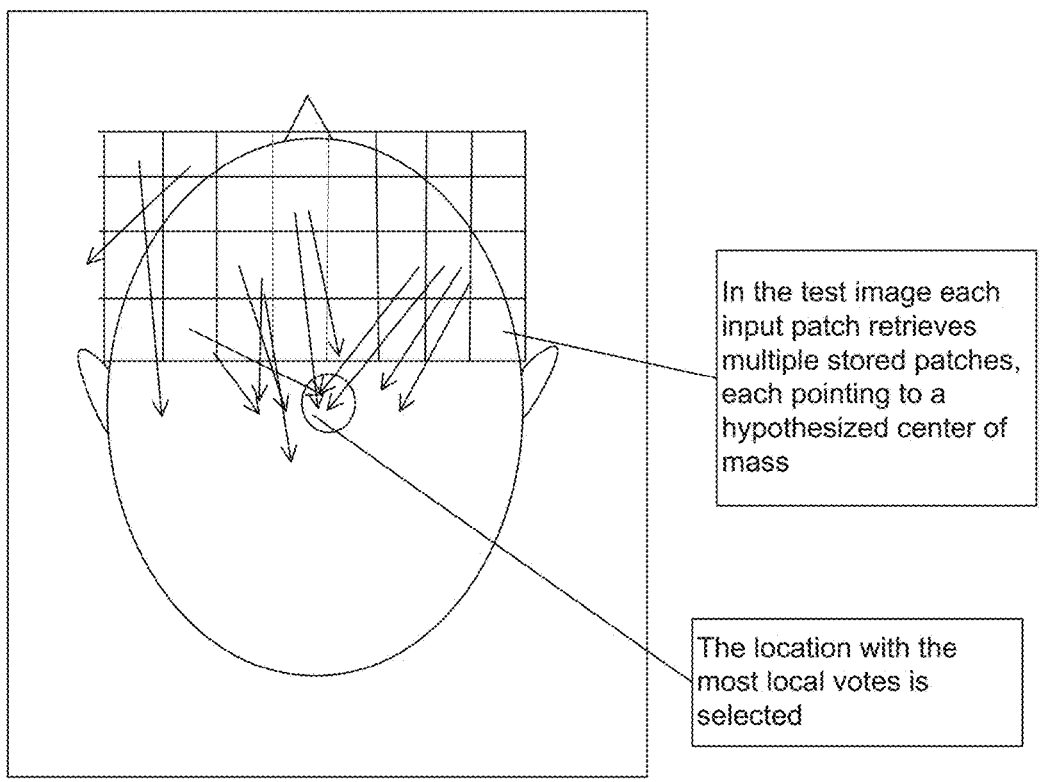
Figure 21:
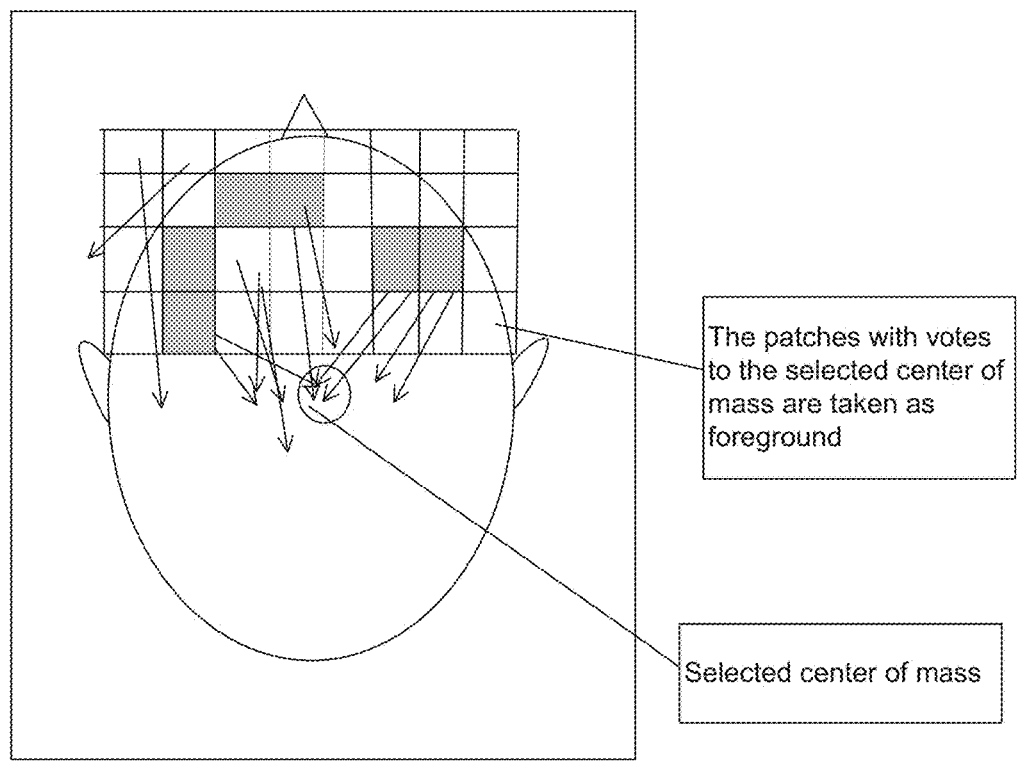
Figure 22:
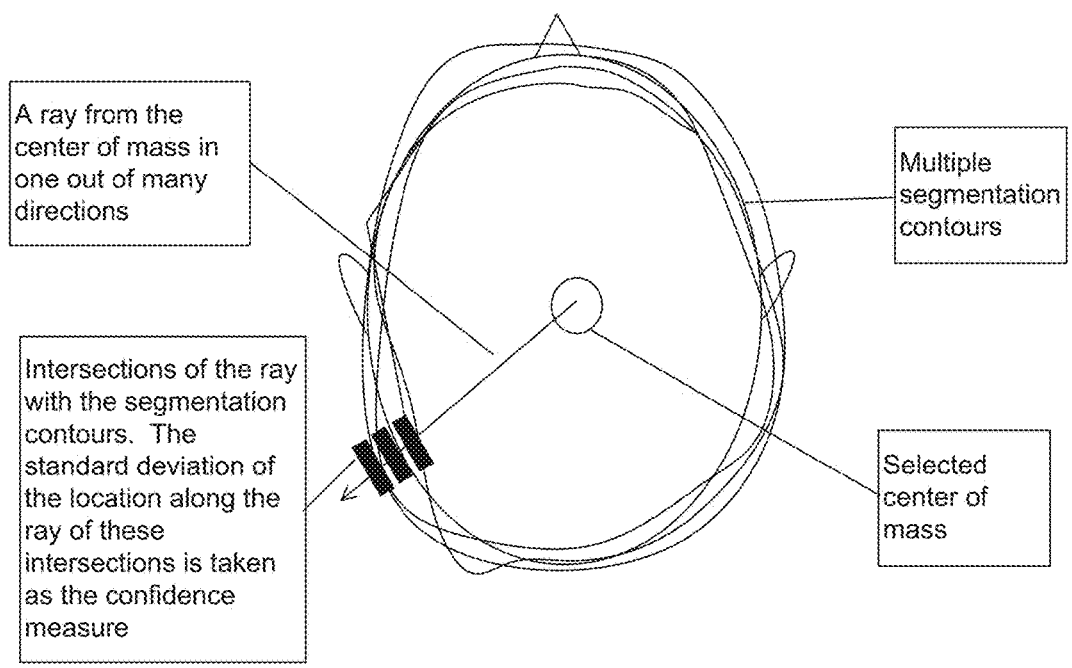

Further regarding the face detection routine, processor 110 may be configured to compare the descriptor vector of each patch in the image information of the subject to descriptor vectors associated with patches of training images to determine a set of the most similar descriptor vectors (e.g., the 25 most similar descriptor vectors). To perform the comparison, processor 110 may be configured to retrieve the descriptor vector of each patch in the image information from memory device 120 and/or from a remote source over a network (e.g., a server or user device), and may be configured to retrieve the descriptor vectors associated with patches of training images from memory device 120 and/or from a remote source over a network (e.g., a server or user device). Processor 110 may be configured to calculate one or more of a Euclidean distance, a Chebyshev distance, a chi-square distance, and a Mahalanobis distance between the descriptor vector of each patch in the image information of the subject and the descriptor vectors associated with patches of training images. The set of the most similar descriptor vectors may include, for example, those descriptor vectors that are associated with a shortest Euclidean distance, Chebyshev distance, chi-square distance, or Mahalanobis distance. The patches associated with the set of the most similar descriptor vectors may be retrieved from the database. Each patch retrieved from the database may provide one vote for a location of the center of mass of the image information of the subject. A vote may be determined by adding a relative location of the center of mass in the training image associated with a given patch to the location of the patch in the image information used to retrieve the patch from the database. A vote, as used in this context, refers to one estimate for a location of the center of mass of the image information of the subject. All votes from all patches of the image information may be integrated and the location with the most support may be selected as the center of mass of the head. FIG. 20 graphically depicts an example of the described voting operations.

In some embodiments, for each patch in the image information of the subject, patches in the set of retrieved patches that point to the selected center of mass location and are within a threshold distance from the selected center of mass may be discarded. The rest are assigned a score that is proportional to two elements: the similarity between the retrieving patch descriptor vector and the retrieved patch descriptor vector, and a distance between the selected center of mass and the center of mass implied by the retrieved patch. For each retrieving patch (i.e., a patch in the image information of the subject), the scores of the retrieved patches may be accumulated. A threshold filter may be applied to the accumulated score of each of the retrieving patches to obtain an initial rough estimate of a foreground region of the head shape in the image information. Processor 110 may be configured to apply one or more morphological operations on the initial rough estimate to produce a closed shape. As graphically depicted, for example, in FIG. 21, the contour of the closed shape may serve as a first segmentation hypothesis. In some embodiments, processor 110 may also be configured to apply a mean shift segmentation algorithm and/or a GrabCut segmentation algorithm to the image information using the first segmentation hypothesis as a starting position for the computation.

In some embodiments, processor 110 may use the contour described above as the detected head or face region. However, in some embodiments, the determination is further refined. For example, in some embodiments a contour of each training image may be represented by a vector containing one or more for the following: (i) the (x, y) coordinates of a number of points (e.g., 50) sampled along the contour at equal distance, wherein the first point is taken, for example, to be the top most point along the contour; (ii) the location of the first point as well as the differences in (x, y) coordinates between every point and the next point (e.g., a number of pairs of (dx, dy) summing up to zero); (iii) the distance of each such contour point from the center of the mass of the contour's captured area and the angle of the ray from the center of mass to a contour point; and (iv) the distances from the center of mass to the points on the contour. To refine the estimated contour of the image information, processor 110 may employ a Principal Components Analysis to compute the Principal Components of the training vectors. The estimated contour may be refined by projecting it onto the space of the Principal Components.

Processor 110 may identify regions in which one or more of the previously determined contours are consistent. For example, densely sampled rays may be projected from the center of mass in all directions. As graphically depicted, for example, in FIG. 22, each ray may intersect the various contours. Processor 110 may be configured to compute the mean and standard deviation of the obtained intersection locations for each ray. If the standard deviation is below a threshold (which may mean that the intersections are nearby and the contours are consistent along the ray), the mean point may be used as a high confidence location for a contour. High confidence locations from a plurality of rays may be grouped into high confidence segments, which may produce a contour that has missing parts and multiple sub-segments. The missing segments may be reconstructed by examining the head shapes in the training images, selecting the head shape that is most consistent with the high confidence segments, and copying the values from the selected head shape into the missing segments.

To detect a number of points in the face region of the image information, processor 110 may be configured to perform a similar voting technique to that described above. For example, while the contour described above is with respect to a head shape or face shape, the same operations may be performed for any other definable contour in the image information of the subject. Processor 110 may be configured, for example, to select points on one or more contours of the image information (e.g., points surrounding the face, eyes, eyebrows, nose, mouth, and/or chin of the subject). For example, processor 110 may be configured to select a number of evenly spaced points along a given contour.

To align the face region, processor 110 may be configured to perform one or more of a translation, rotation, and scaling operation such that the resulting face is maximally aligned with an average face model. In some embodiments, regions of interest may be determined based on their known association to corresponding facial regions determined based on the detected points. The regions of interest may then be aligned to the average face model.

Processor 110 may be configured to perform a first evaluation of the external soft tissue image information using at least one of an anchored cell analysis, a shifting patches analysis, and a relative measurements analysis (step 220). To perform the anchored cell analysis, processor 110 may be configured to overlay a grid with a plurality of cells on the external soft tissue information, calculate descriptors for each of the plurality of cells, aggregate the descriptors to produce a vector, and compare the vector to previously produced vectors from external soft tissue images of other individuals previously diagnosed with the medical condition.

Figure 23C:
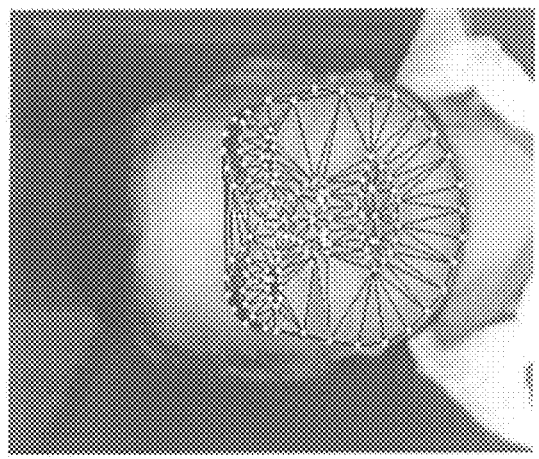
FIGS. 23A-23C illustrate exemplary depictions of an anchored cell analysis in accordance with some of the disclosed embodiments.
Figure 23B:
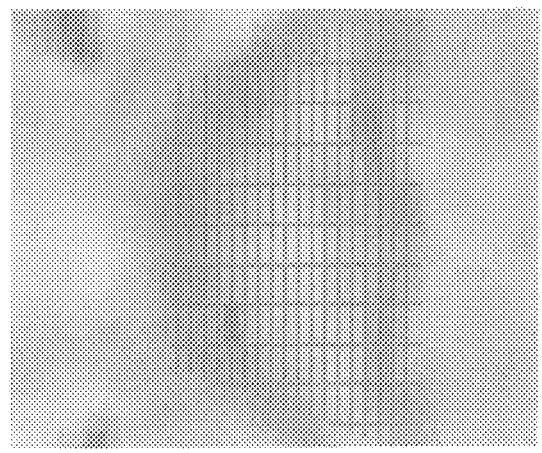
Figure 23A:
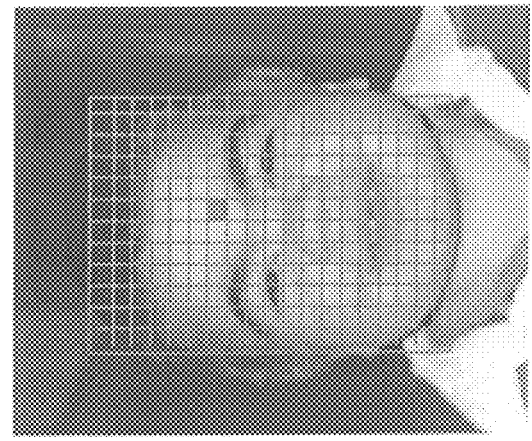

Overlaying the grid of cells may include a number of different complementary and/or alternative options. For example, as depicted in FIG. 23A, processor 110 may be configured to overlay a fixed grid with a plurality of cells on the external soft tissue image information. A fixed grid of cells may include, for example, a plurality of adjacent squares, rectangles, or triangles that are overlaid on a region (e.g., a face region) of the external soft tissue image information. As another example, as depicted in FIG. 23B, processor 110 may be configured to overlay a small grid of cells, which may be smaller in size than the cells of the fixed grid discussed above, on a particular defined region, such as at least one of a forehead region, a periorbital region, a nasal region, a mid-face region, an ear region, and an oral region of the external soft tissue image information; processor 110 may be configured to discount at least one other region of the external soft tissue image information (e.g., a region from which minimal, or no, relevant information can be obtained, such as a hair region, may not be overlaid with a small grid of cells). As another example, as depicted in FIG. 23C, processor 110 may also be configured to overlay a plurality of triangle cells generated by connecting points detected on the external soft tissue image information. For example, processor 110 may determine a plurality of feature points on the image information and connect the feature points to form triangular regions.

To calculate descriptors for each of the plurality of cells, processor 110 may be configured, for example, to analyze at least one of an intensity, a texture, and an edge associated with the external soft tissue image information. In some embodiments, the descriptor for each cell is a vector that includes, for example, data derived from at least one of a SIFT, HOG, a self-similarity descriptor, a histogram of Local Binary Patterns, and any other type of feature used in image analysis and computer vision. In some embodiments, the descriptor for each cell may be a vector that includes, for example, data derived from at least one layer in a neural network.

To aggregate the descriptors to produce a vector, processor 110 may be configured, for example, to create a vector that includes one or more of the calculated descriptors. For example, each of the descriptors associated with a cell in a fixed grid may be aggregated into a vector, each of the descriptors associated with a set of triangle cells may be aggregated into a vector, or each of the descriptors associated with a small grid of cells may be aggregated into a vector. Additionally or alternatively, if more than one set of cells is created (e.g., both a fixed grid and a set of triangle cells are formed, both a fixed grid and a small grid of cells are formed, both a set of triangle cells and a fixed grid are formed, or a fixed grid, set of triangle cells, and small grid are all formed), a single vector may be created that includes the descriptors of multiple sets of cells. Additionally or alternatively, more than one cell may be combined together to a plurality of additional descriptors, which also may be combined to form another level of representation, such as a plurality of layers in a neural network. The vector that includes the aggregated descriptors may be referred to as, for example, a combined appearance vector.

To compare the vector to previously produced vectors from external soft tissue images of other individuals previously diagnosed with the medical condition, processor 110 may be configured, for example, to access a database. The database may include, for example, vectors produced using an anchored cell analysis of external soft tissue images of other individuals. The database may be annotated by one or more of patient ID, age, age group, gender, ethnic group, race group, dysmorphic feature, phenotypic feature, anthropometric measurements (including without limitation, height, weight, head circumference, facial height, skull height, upper facial height, lower facial height, head length, head width, facial width, mandibular width, anterior fontanelle size, posterior fontanelle size, inner canthal distance, outer canthal distance, interpupillary distance, interorbital distance, palpebral fissure length, palpebral fissure height, obliquity of the palpebral fissure, orbital protrusion, corneal dimensions, ear length, ear width, ear protrusion, ear position, ear rotation, nasal height, length of the columella, nasal protrusion, nasal width, philtrum length, philtrum width, mouth width, ONC angle, maxillomandibular differential, and mandible width), relative ratios and proportions between bodily and facial landmarks, known diagnosis, suspected diagnosis, mutations and/or genetic variants, source of image, informed consent, pose, illumination, quality of image, expression type, and association with cohort (e.g., part of a control group of individuals known not to be affected by a medical condition or part of a group of individuals known to be affected by a medical condition). The database may also be annotated by, for example, linking data regarding individuals in the database that are family members (e.g., siblings, parents, children, cousins, etc.) and/or indicating the relationship of other family members in the database that are affected by a medical condition or dysmorphic feature to an individual (e.g., sister of grandmother from the mother's side). In some embodiments, the previously produced vectors used in the comparison are associated with one or more annotations that are in common. For example, the previously produced vectors may be associated with an annotation indicating that they were derived from images associated with individuals of the same age, gender, and ethnicity as the subject. Additionally or alternatively, previously produced vectors used in the comparison may be associated with a suspected dysmorphic feature and/or a suspected medical condition of the subject. That is, for example, the previously produced vectors may be associated with one or more of individuals affected by a dysmorphic feature, individuals in a control group for the dysmorphic feature, individuals affected by a medical condition, and individuals in a control group for the medical condition. Additionally or alternatively, the previously described image cells may be used as an input for a neural network to perform an association to an annotated database.

Data associated with a set of the most similar previously produced vectors (e.g., the 25 most similar previously produced vectors) may be determined. For example, processor 110 may be configured to calculate one or more of a Euclidean distance, a Chebyshev distance, a chi-square distance, a Mahalanobis distance, or other descriptor metrics, such as intersection kernel cosine similarity, or any other distance metric, including a metric that learned from a database to optimize the metric separability between at least two classes between the combined appearance vector and the previously produced vectors in the database to determine a set of the most similar previously produced vectors (e.g., the 25 previously produced vectors associated with the 25 shortest computed distances may be selected).

The set of the most similar previously produced vectors may be analyzed (at, for example, a server associated with the database or by processor 110) to determine how many of the previously produced vectors are associated with a positive example of a particular dysmorphic feature (that is, a previously produced vector associated with an individual known to have the dysmorphic feature) and how many of the previously produced vectors are associated with a negative example of a particular dysmorphic feature (that is, a previously produced vector associated with an individual known to not have the dysmorphic feature). Based on the number of positive examples and the number of negative examples, a probability score may be determined for the dysmorphic feature. A probability score may be calculated also based on the correspondence of the previously produced vectors fused into at least one statistical or other model, learned on the previous calculated database. Such a model may capture the relevant information needed to associate the test vector to at least one class from the database. Association may be achieved using a probability per class or an association to a specific class directly. A probability score, as used herein, may be an actual probability or some value that is reflective of a probability. For example, a probability score may provide some indication of the likelihood that a subject has a dysmorphic feature. For example, if only positive examples are included in the set of most similar previously presented vectors, a very high or maximum probability score may be determined (e.g., a probability score of 100). If only negative examples are included, then a very low probability score may be determined (e.g., a probability score of 1). If a mixture of positive and negative examples is included, then the probability score may reflect the number of positive examples and the number of negative examples. The probability score may or may not be directly proportional to the number of positive and negative examples. For example, in some embodiments, if a threshold number of positive examples are obtained, then the same very high or maximum probability score may be determined regardless of the number of positive examples or negative examples. Moreover, a probability score is not necessarily a positive value. In some embodiments, the probability score may be a negative score. Moreover, all of the probability scores do not necessarily add up to 100%. In some embodiments, a probability score may be any real valued score that is approximately monotonic with respect to the underlying probability of a certain medical condition or dysmorphology.

In some embodiments, a probability score for the dysmorphic feature may also, or alternatively, be calculated based on a degree of similarity of the combined appearance vector to a given one of the previously produced vectors. For example, if an equal number of positive and negative examples are retrieved, but the combined appearance vector is more similar to the previously produced vectors associated with positive examples than the previously produced vectors associated with negative examples, then the probability score may be relatively high. In contrast, if an equal number of positive and negative examples are retrieved, but the combined appearance vector is more similar to the previously produced vectors associated with negative examples than the previously produced vectors associated with positive examples, then the probability score may be relatively low.

In some embodiments, processor 110 may calculate more than one probability score for a given dysmorphic feature. For example, one probability score may be determined by treating all positive and negative examples equally, and another probability score may be determined that considers the similarity of the combined appearance vector to the positive and negative samples. Moreover, probability scores for a plurality of different dysmorphic features may be calculated in the same or substantially the same way.

While the above anchored cell analysis description refers to dysmorphic features, the same process may also, or alternatively, be performed to determine probability scores for one or more medical conditions. For example, rather than determining the association of previously presented vectors to dysmorphic features, processor 110 may determine which medical conditions are associated with the previously presented vectors.

To perform the shifting patches analysis, processor 110 may be configured to overlay a plurality of densely spaced or overlapping patches on the external soft tissue image information, calculate a descriptor vector for each of the plurality of patches, and compare each descriptor vector to previously produced vectors from a similar region in external soft tissue images of other individuals previously determined to be affected by the medical condition.

Figure 24:
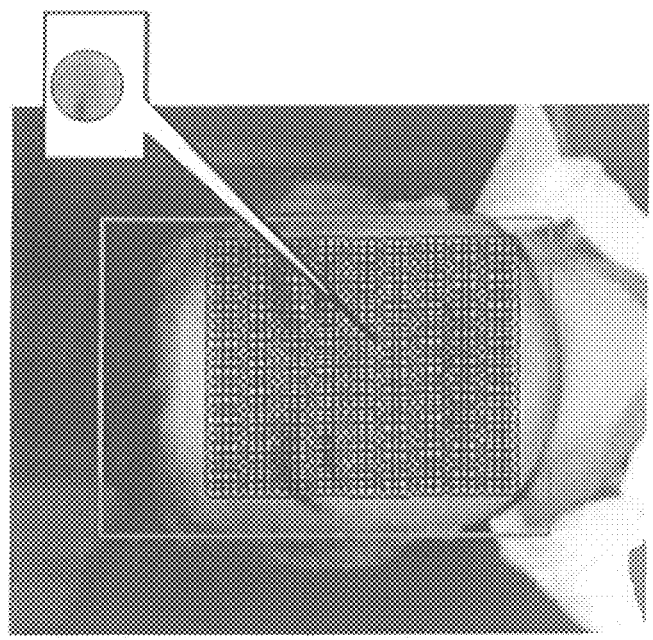
FIG. 24 illustrates exemplary depictions of a shifting patch analysis in accordance with some of the disclosed embodiments.

As depicted in FIG. 24, to overlay patches on the external soft tissue image information, processor 110 may be configured, for example, to overlay multiple densely spaced or overlapping patches, which optionally may be of varying sizes, onto a region of the image information (e.g., a face region). For example, a square patch of a first size may be overlaid on the region of the image information at every possible position (e.g., the square patch may be shifted by one pixel in every direction until the patch is overlaid in every possible position) or at a subset of the possible positions (e.g., the square patch may be shifted by ten pixels in every direction in every direction until the patch is overlaid over the entire region of the image information). In some embodiments, a square patch of one or more different sizes may also be overlaid on the region of the image information.

To calculate a descriptor vector for each of the plurality of patches, processor 110 may be configured to compute, for example, data derived from at least one of a scale-invariant feature transform (SIFT), a histogram of oriented gradients (HOG), a self-similarity descriptor, a histogram of Local Binary Patterns, and any other type of feature used in image analysis and computer vision. In some embodiments, the descriptor for each cell is a vector that includes, for example, data derived from a at least one layer in a neural network.

To compare each descriptor vector to previously produced vectors from a similar region in external soft tissue images of other individuals previously determined to be affected by the medical condition, processor 110 may be configured to access a database. For example, the same database discussed above with respect to the anchored cell analysis, or a similar database, may include previously produced vectors for patches of images of individuals previously determined to be affected by the medical condition. As described above, the database may annotate the previously produced vectors with a variety of data such as, for example, one or more of patient ID, age, age group, gender, ethnic group, race group, dysmorphic feature, phenotypic feature, anthropometric measurements (including without limitation, height, weight, head circumference, facial height, skull height, upper facial height, lower facial height, head length, head width, facial width, mandibular width, anterior fontanelle size, posterior fontanelle size, inner canthal distance, outer canthal distance, interpupillary distance, interorbital distance, palpebral fissure length, palpebral fissure height, obliquity of the palpebral fissure, orbital protrusion, corneal dimensions, ear length, ear width, ear protrusion, ear position, ear rotation, nasal height, length of the columella, nasal protrusion, nasal width, philtrum length, philtrum width, mouth width, ONC angle, maxillomandibular differential, and mandible width), relative ratios and proportions between bodily and facial landmarks, known diagnosis, suspected diagnosis, mutations and/or genetic variants, source of image, informed consent, pose, illumination, quality of image, expression type, and association with cohort (e.g., part of a control group of individuals known not to be affected by a medical condition or part of a group of individuals known to be affected by a medical condition). The database may also be annotated by, for example, linking data regarding individuals in the database that are family members (e.g., siblings, parents, children, cousins, etc.) and/or indicating the relationship of other family members in the database that are affected by a medical condition or dysmorphic feature to an individual (e.g., sister of grandmother from the mother's side).

Processor 110 may compare one or more of the descriptor vectors associated with the patches of the image information with the previously produced vectors in the database. The comparison may occur at a server associated with the database, or may occur directly by processor 110 using, for example, information retrieved from the database. The previously produced vectors used in the comparison may be from a similar region as the descriptor vector in external soft tissue images of other individuals previously determined to be affected by one or more medical conditions and of other individuals in a control group. A similar region may include, for example, a patch in image information in the database that is the same, or substantially the same, distance from a center of mass of a face in the same or substantially the same direction. A similar region may also include, for example, a patch in image information in the database that is associated with a same organ or type of region as a patch associated with a respective descriptor vector associated with the image information of the subject. For example, if the descriptor vector associated with a particular patch of the image information of the subject is within an nose region, the descriptor vector may be compared to one or more descriptor vectors in the database that are also associated with a nose region. In some embodiments, only patches in the database that point to a center of mass location that is not relatively far away from the center of mass of the face region of the image information and/or a center of mass of a particular organ or type of region are considered. Additionally or alternatively, the previously produced vectors may be used as part of a neural network to perform an association to an annotated database.

In some embodiments, the descriptor vector may be compared only to previously produced vectors that are associated with one or more annotations that are in common. For example, the previously produced vectors used in the comparison may be associated with an annotation indicating that they were derived from images associated with individuals of the same age, gender, and weight. Additionally or alternatively, the previously produced vectors used in the comparison may be associated with a suspected dysmorphic feature and/or a suspected medical condition. That is, for example, the previously produced vectors may be associated with one or more of individuals affected by a dysmorphic feature, individuals in a control group for the dysmorphic feature, individuals affected by a medical condition, and individuals in a control group for the medical condition.

Data associated with a set of the most similar previously produced vectors in the database (e.g., the 25 most similar previously produced vectors) may be determined. For example, processor 110 may be configured to calculate one or more of a Euclidean distance, a Chebyshev distance, a chi-square distance, a Mahalanobis distance, or other descriptor metrics, such as intersection kernel cosine similarity, or any other distance metric, including a metric that learned from a database to optimize the metric separability between at least two classes, between each descriptor vector and the previously produced vectors in the database to determine a set of the most similar previously produced vectors (e.g., the 25 previously produced vectors associated with the 25 shortest computed distances may be selected). Data associated with the set of the most similar previously produced vectors for each descriptor vector may be determined. The data may include, for example, one or more dysmorphic features and/or one or more medical conditions associated with the set of the most similar previously produced vectors.

The set of the most similar previously produced vectors may be analyzed (at, for example, a server associated with the database or by processor 110) to determine how many of the previously produced vectors are associated with a positive example of a particular dysmorphic feature (that is, a previously produced vector associated with an individual known to have the dysmorphic feature) and how many of the previously produced vectors are associated with a negative example of a particular dysmorphic feature (that is, a previously produced vector associated with an individual known to not have the dysmorphic feature). Based on the number of positive examples and the number of negative examples, a probability score may be determined for the dysmorphic feature. For example, if only positive examples are retrieved, a very high or maximum probability score may be determined (e.g., a probability score of 100). If, for example, only negative examples are retrieved, a very low probability score may be determined (e.g., a probability score of 1). If a mixture of positive and negative examples is determined then the probability score may reflect the number of positive examples and the number of negative examples. However, the probability score may or may not be directly proportional to the number of positive and negative examples. For example, if a threshold number of positive examples are obtained, then in some embodiments the same very high or maximum probability score as if only positive examples were found may be determined A probability score may be calculated also based on the correspondence of the previously produced vectors fused into at least one statistical or other model, learned on the previously calculated database. Such a model may capture the relevant information needed to associate the test vector to at least one class from the database. Association may be achieved using a probability per class or an association to a specific class directly.

In some embodiments, a probability score for the dysmorphic feature may also, or alternatively, be calculated based on a degree of similarity of the descriptor vector to a given one of the previously produced vectors. For example, if an equal number of positive and negative examples are retrieved, but the descriptor vector is more similar to the previously produced vectors associated with positive examples than the previously produced vectors associated with negative examples, then the probability score may be relatively high. In contrast, if an equal number of positive and negative examples are retrieved, but the descriptor vector is more similar to the previously produced vectors associated with negative examples than the previously produced vectors associated with positive examples, then the probability score may be relatively low. Thus, more than one probability score may be calculated for a given dysmorphic feature. Moreover, probability scores for a plurality of different dysmorphic features may be calculated in the same or substantially the same way.

In some embodiments, a probability score for a dysmorphic feature may also depend on a degree to which a center of mass associated with the patch associated with the descriptor vector corresponds to a center of mass associated with a patch associated with a particular previously produced vector. For example, a center of mass of a face of the subject may be a first distance and direction from the patch associated with the descriptor vector, and a center of mass of a face in a previously presented image may be a second distance and direction from a patch associated with the particular previously produced vector. The data associated with the particular previously produced vector (e.g., whether it comes from a positive or negative example of a dysmorphic feature) may have more or less significance on the probability score based on the degree to which the two distances and directions correspond.

While the above shifting patch analysis description refers to dysmorphic features, the same process may also, or alternatively, be performed to determine probability scores for one or more medical conditions. For example, rather than determining the association of previously presented vectors to dysmorphic features, processor 110 may determine which medical conditions are associated with the previously presented vectors.

To perform the relative measurements analysis, processor 110 may be configured to calculate a plurality of relative measurements between a plurality of locations within the external soft tissue image information, aggregate the plurality of measurements to produce a vector for the plurality of measurements, and compare the vector to previously produced vectors from external soft tissue images of other individuals previously determined to be affected by the medical condition.

Figure 25:
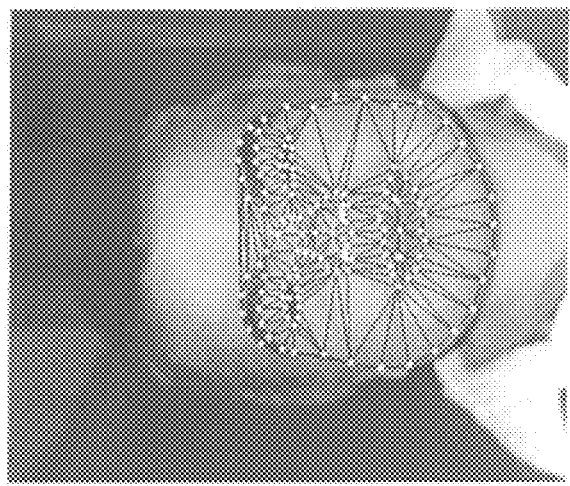
FIG. 25 illustrates exemplary depictions of a relative measurements analysis in accordance with some of the disclosed embodiments.

To calculate a plurality of relative measurements between a plurality of locations within the external soft tissue image information, processor 110 may be configured to detect a plurality of feature points in the external soft tissue image information. For example, as depicted in FIG. 25, a plurality of points in a face region of the image information may be detected, including, for example, one or more points surrounding eye regions, eyebrow regions, a nose region, a mouth region, and a chin region of the image information. These feature points may be detected using, for example, the operations described above.

Using the feature points, a plurality of relative measurements may be calculated. The plurality of relative measurements may include, for example, one or more distances between feature points, angles formed by sets of feature points, sizes of areas formed by sets of feature points, shapes defined by sets of feature points, ratios established by sets of distances, angles, and sizes, and any other relative measurement that may be performed using the detected feature points. Other relative measurements may include, for example, any of the measurements disclosed in "Handbook of normal physical measurements," 2nd edition, 2009, Oxford University Press, to Hall et al., which is incorporated herein by reference in its entirety.

To aggregate the plurality of measurements to produce a vector for the plurality of measurements, processor 110 may be configured create a vector that includes one or more of the calculated relative measurements. For example, each of the relative measurements may be aggregated into a single vector or each of the relative measurements of a certain type (e.g., relative measurements relating to distance measurements) may be aggregated into a vector.

To compare the vector to previously produced vectors from external soft tissue images of other individuals previously determined to be affected by the medical condition, processor 110 may be configured to access a database. For example, the same database discussed above with respect to the anchored cell analysis and the shifting patch analysis, or a similar database, may include previously produced vectors for relative measurements of individuals previously determined to be affected by the medical condition. As described above, the database may annotate the previously produced vectors with a variety of data such as, for example, one or more of patient ID, age, age group, gender, ethnic group, race group, dysmorphic feature, phenotypic feature, anthropometric measurements (including without limitation, height, weight, head circumference, facial height, skull height, upper facial height, lower facial height, head length, head width, facial width, mandibular width, anterior fontanelle size, posterior fontanelle size, inner canthal distance, outer canthal distance, interpupillary distance, interorbital distance, palpebral fissure length, palpebral fissure height, obliquity of the palpebral fissure, orbital protrusion, corneal dimensions, ear length, ear width, ear protrusion, ear position, ear rotation, nasal height, length of the columella, nasal protrusion, nasal width, philtrum length, philtrum width, mouth width, ONC angle, maxillomandibular differential, and mandible width), relative ratios and proportions between bodily and facial landmarks, known diagnosis, suspected diagnosis, mutations and/or genetic variants, source of image, informed consent, pose, illumination, quality of image, expression type, and association with cohort (e.g., part of a control group of individuals known not to be affected by a medical condition or part of a group of individuals known to be affected by a medical condition). The database may also be annotated by, for example, linking data regarding individuals in the database that are family members (e.g., siblings, parents, children, cousins, etc.) and/or indicating the relationship of other family members in the database that are affected by a medical condition or dysmorphic feature to an individual (e.g., sister of grandmother from the mother's side).

Processor 110 may compare an aggregated vector of relative measurements with the previously produced vectors in the database. The comparison may occur at a server associated with the database, or may occur directly by processor 110 using, for example, information retrieved from the database.

In some embodiments, the previously produced vectors used in the comparison may be associated with one or more annotations that are in common. For example, the previously produced vectors used in the comparison may be associated with an annotation indicating that they were derived from images associated with individuals of the same age, gender, and weight. Additionally or alternatively, the previously produced vectors used in the comparison may be associated with a suspected dysmorphic feature and/or a suspected medical condition. That is, for example, the previously produced vectors used in the comparison may be associated with one or more of individuals affected by a dysmorphic feature, individuals in a control group for the dysmorphic feature, individuals affected by a medical condition, and individuals in a control group for the medical condition.

Data associated with a set of the most similar previously produced vectors in the database (e.g., the 25 most similar previously produced vectors) may be determined for at least one aggregated vector of relative measurements. For example, processor 110 may be configured to calculate one or more of a Euclidean distance, a Chebyshev distance, a chi-square distance, a Mahalanobis distance, or other descriptor metrics, such as intersection kernel cosine similarity, or any other distance metric, including a metric that learned from a database to optimize the metric separability between at least two classes between the aggregated vector of relative measurements and the previously produced vectors in the database to determine a set of the most similar previously produced vectors (e.g., the 25 previously produced vectors associated with the 25 shortest computed distances may be selected). The data associated with the set of the most similar previously produced vectors may include, for example, one or more dysmorphic features and/or one or more medical conditions associated with the set of the most similar previously produced vectors. For example, for each aggregated vector of relative measurements, one or more dysmorphic features associated with a predefined number of the most similar previously produced vectors may be determined Additionally or alternatively, for each aggregated vector of relative measurements, one or more medical conditions associated with a predefined number of the most similar previously produced vectors may be determined.

The set of the most similar previously produced vectors may be analyzed (at, for example, a server associated with the database or by processor 110) to determine how many of the previously produced vectors are associated with a positive example of a particular dysmorphic feature (that is, a previously produced vector associated with an individual known to have the dysmorphic feature) and how many of the previously produced vectors are associated with a negative example of a particular dysmorphic feature (that is, a previously produced vector associated with an individual known to not have the dysmorphic feature). Based on the number of positive examples and the number of negative examples, a probability score may be determined for the dysmorphic feature. A probability score may be calculated also based on the correspondence of the previously produced vectors fused into at least one statistical or other model, learned on the previously calculated database. Such a model may capture the relevant information needed to associate the test vector to at least one class from the database. Association may be achieved using a probability per class or an association to a specific class directly. For example, if only positive examples are retrieved, a very high or maximum probability score may be determined (e.g., a probability score of 100). If, for example, only negative examples are retrieved, a very low probability score may be determined (e.g., a probability score of 1). If a mixture of positive and negative examples is determined then the probability score may reflect the number of positive examples and the number of negative examples. However, the probability score may or may not be directly proportional to the number of positive and negative examples. For example, if a threshold number of positive examples are obtained, then in some embodiments the same very high or maximum probability score as if only positive examples were found may be determined.

In some embodiments, a probability score for the dysmorphic feature may also, or alternatively, be calculated based on a degree of similarity of the aggregated vector of relative measurements to a given one of the previously produced vectors. For example, if an equal number of positive and negative examples are retrieved, but the aggregated vector of relative measurements is more similar to the previously produced vectors associated with positive examples than the previously produced vectors associated with negative examples, then the probability score may be relatively high. In contrast, if an equal number of positive and negative examples are retrieved, but the aggregated vector of relative measurements is more similar to the previously produced vectors associated with negative examples than the previously produced vectors associated with positive examples, then the probability score may be relatively low. Thus, more than one probability score may be calculated for a given dysmorphic feature. Moreover, probability scores for a plurality of different dysmorphic features may be calculated in the same or substantially the same way.

In some embodiments, the comparison to previously produced vectors may not be a direct comparison. For example, the previously produced vectors may be analyzed to determine percentiles regarding various relative measurements in a population. Processor 110 may determine where various relative measurements in the aggregated vector of relative measurements fall in a particular population. Processor 110 may, for example, determine the percentile of a particular dysmorphic feature of the subject in a population (e.g., the length of a facial feature is compared to a population). The population may be a general population or may be some subset defined by, for example, an aspect of the subject (e.g., the subject's age, gender, ethnicity, etc.) Based on the percentile, processor 110 may determine whether the subject is likely to exhibit a dysmorphic feature and determine a probability score of the dysmorphic feature. Processor 110 may also, or alternatively, be configured to determine a severity score associated with a dysmorphic feature. For example, if processor 110 determines that the subject is likely to exhibit a dysmorphic feature, a determination may be made as to a severity score based on the determined percentile associated with the subject.

As another example of an indirect comparison, in some embodiments, one or more dysmorphic features may be defined directly by one or more relative measurements. For example, an analysis of the previously produced vector may demonstrate that a triangular face dysmorphic feature or an up-slanting eye dysmorphic feature may be defined by one or more angles or ranges of angles defined by a set of feature points. Thus, processor 110 may, for example, compare an aggregated vector of relative measurements to a defined dysmorphic feature. A probability score may be determined based on whether or not the aggregated vector of relative measurements satisfies the defined dysmorphic feature and/or a degree to which the aggregated vector of relative measurements satisfies the defined dysmorphic feature. Processor 110 may also, or alternatively, be configured to determine a severity score associated with a dysmorphic feature. For example, if processor 110 determines that the subject is likely to exhibit a dysmorphic feature, a determination may be made as to a severity score based on the degree to which the aggregated vector of relative measurements satisfies the defined dysmorphic feature. The probability score and/or the severity score determined using the relative measurements may be determined based on a normalization procedure. For example, in some embodiments, the lengths of mouth-related measurements may be normalized based on the width of the face. The normalized measurements may then be analyzed using the defined dysmorphic features.

While the above relative measurement analysis description refers to dysmorphic features, the same process may also, or alternatively, be performed to determine probability scores for one or more medical conditions. For example, rather than determining the association of previously produced vectors to dysmorphic features, processor 110 may determine which medical conditions are associated with the previously produced vectors.

Figure 26:
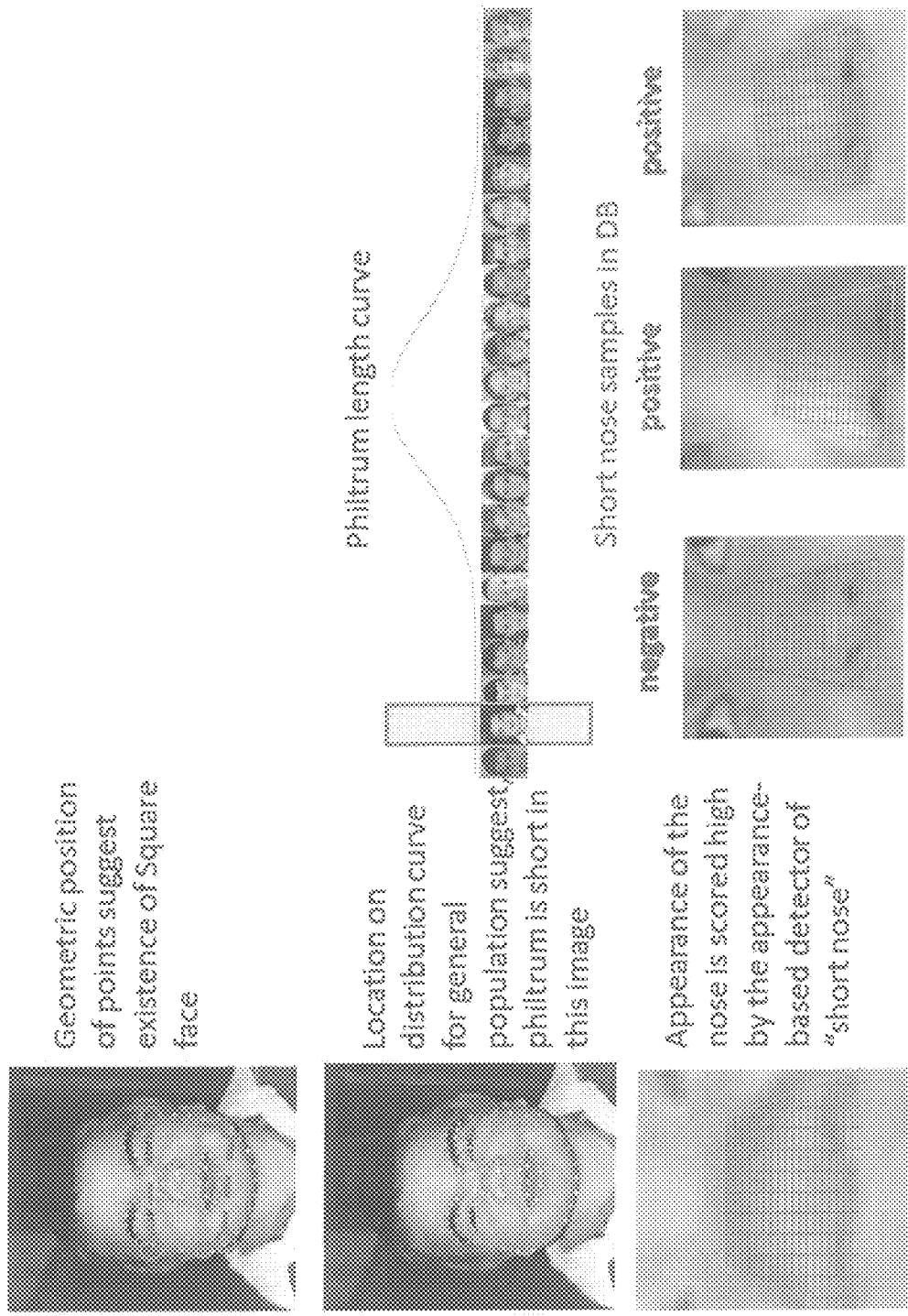
FIG. 26 illustrates exemplary depictions of a plurality of analyses in accordance with some of the disclosed embodiments.

FIG. 26 depicts an example of each of the three techniques that may be used for relative measurements analysis. For example, the geometric position of the feature points may define a square face dysmorphic feature. The location on a philtrum length distribution curve may suggest that the subject has a short philtrum. The aggregated vector of relative measurements may be most similar to two positive examples of a short nose and one negative example of a short nose.

Processor 110 may be configured to generate first evaluation result information based, at least in part, on the first evaluation (step 230). Processor 110 may utilize the data derived from the first evaluation to generate the first evaluation result. For example, as discussed above, one or more probability scores for one or more dysmorphic features and/or one or more medical conditions may be determined in the first evaluation. If a plurality of probability scores for any particular dysmorphic feature and/or any particular medical condition are determined in the first evaluation, then the probability scores for the particular dysmorphic feature and/or the particular medical condition may be combined. As one example, an average of the probability scores may be determined. As another example, the plurality of probability scores for a particular dysmorphic feature and/or a particular medical condition may be input into a classifier that is calibrated to output another probability score attributed to the particular dysmorphic feature and/or the particular medical condition. For example, the classifier may be trained with positive and negative examples of a medical condition in order to determine a single probability score and/or severity score of a particular dysmorphic feature and/or a particular medical condition based on a received set of probability scores. In some embodiments, the classifier may also, or alternatively, be configured to receive a set of severity scores in order to determine a probability score for the medical condition.

Processor 110 may be configured to perform a second evaluation of the external soft tissue image information using at least one of the anchored cell analysis, the shifting patches analysis, and the relative measurements analysis (step 240). For example, if the first evaluation includes an anchored cell analysis, then a shifting patches analysis or relative measurements analysis may be performed as the second evaluation. If the first evaluation includes a shifting patches analysis, then an anchored cell analysis or relative measurements analysis may be performed. If the first evaluation includes a relative measurements analysis, then an anchored cell analysis or shifting patches analysis may be performed as the second evaluation. The anchored cell analysis, shifting patches analysis, and relative measurements analysis may be performed in the same or substantially the same manner as described above with respect to step 220.

In some embodiments, the first evaluation and second evaluation may be of the same general type (e.g., both may be an anchored cell analysis, both may be a shifting patches analysis, or both may be relative measurements analysis). In such embodiments, one of the evaluations may result in, for example, one or more probability scores associated with one or more dysmorphic features, whereas another one of the evaluations may result in, for example, one or more probability scores associated with one or more medical conditions. Likewise, even if the general types of analysis are different, one of the evaluations may result in, for example, one or more probability scores associated with one or more dysmorphic features, whereas another one of the evaluations may result in, for example, one or more probability scores associated with one or more medical conditions.

Processor 110 may be configured to generate second evaluation result information based, at least in part, on the second evaluation (step 250). Processor 110 may utilize the data derived from the second evaluation to generate the second evaluation result. For example, one or more probability scores and/or severity scores for one or more dysmorphic features and/or one or more medical conditions may be determined in the second evaluation that are combined using one or more classifiers to generate a single probability score associated with one or more particular dysmorphic features and/or medical conditions.

Processor 110 may be configured to predict a likelihood that the subject is affected by the medical condition based, at least in part, on the first evaluation result information and the second evaluation result information (step 260). For example, if the first evaluation result information includes one or more probability scores associated with one or more dysmorphic features, and the second evaluation result information includes one or more probability scores associated with one or more dysmorphic features, processor 110 may be configured to analyze the information to determine the likelihood. Alternatively, for example, if the first evaluation result information includes one or more probability scores associated with one or more medical conditions, and the second evaluation result information includes one or more probability scores associated with one or more medical conditions, processor 110 may be configured to analyze the information to determine the likelihood. Alternatively, for example, if the first evaluation result information includes one or more probability scores associated with one or more medical conditions, and the second evaluation result information includes one or more probability scores associated with one or more dysmorphic features, processor 110 may be configured to analyze the information to determine the likelihood. Likewise, if, for example, the first evaluation result information includes one or more probability scores associated with one or more dysmorphic features, and the second evaluation result information includes one or more probability scores associated with one or more medical conditions, processor 110 may be configured to analyze the information to determine the likelihood.

If both evaluations return a set of probability scores for a set of dysmorphic features, then the set of probability scores for the set of dysmorphic features may be input into a trained classifier that is calibrated to output a probability score attributed to a particular medical condition. For example, the classifier may be trained with positive and negative examples of the medical condition in order to determine a probability score of the particular medical condition.

If both evaluations return a set of probability scores for a set of medical conditions, then the set of probability scores for a particular medical condition may be input into a trained classifier that is calibrated to output another probability score attributed to the particular medical condition. For example, the classifier may be trained with positive and negative examples in order to determine a probability score of the particular medical condition. In this way, a more accurate medical condition probability score may be determined than any one of the individual evaluations that produced a medical condition likelihood.

If one of the evaluations returns a set of probability scores for a set of dysmorphic features and another one of the evaluations results a set of probability scores for a medical condition, then the set of probability scores for the set of dysmorphic features from one evaluation and the set of probability scores for a particular medical condition from the other evaluation, may be input into a trained classifier that is calibrated to output another probability score attributed to a particular medical condition. For example, the classifier may be trained with positive and negative examples of a medical condition in order to determine a probability score of the particular medical condition.

In some embodiments an initial determination of the likelihood that the subject is affected by the medical condition may be revised. For example, a likelihood of a plurality of medical conditions may initially be determined. Then, a revised likelihood of one or more of the medical conditions may be determined based on the other likelihoods. For example, if two medical conditions are related such that they typically occur together, a low probability score for one medical condition may decrease an otherwise high probability score for the other medical condition. Similarly, if two medical conditions are related such that they typically do not occur together, a high probability score for both medical conditions may cause both probability scores to decrease. Moreover, for example, if a set of medical conditions are initially determined to have a high probability score, but are known to commonly be misdiagnosed for another medical condition, then the probability score of each medical condition in the set may be decreased and the probability score of the other medical condition may be increased.

Processor 110 may be configured to consider other data as well when determining the likelihood of the medical condition. For example, more than two evaluations may be performed in substantially the same manner as the first and second evaluations described above. Processor 110 may be configured to analyze the additional evaluations using the techniques described above. Moreover, features associated with the subject may be determined from other sources. For example, a physician may provide (e.g., dictate or type) one or more known features (e.g., dysmorphic features, biographical information, demographic information, etc.) of the subject that are used, for example, to limit the images in the database that the subject is compared to (e.g., the subject may only be compared against other individuals sharing one or more of the features provided by the physician).

Figure 3:
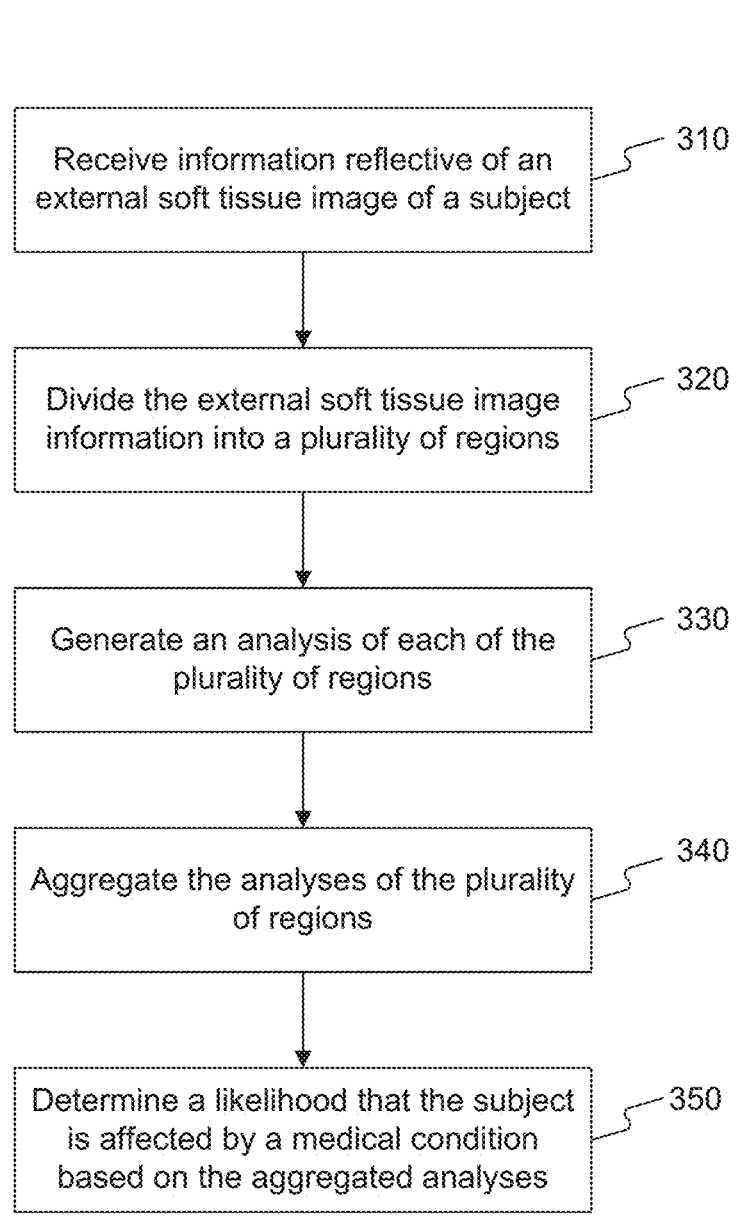
FIG. 3 illustrates example operations that a processor of a medical condition analysis system may be configured to perform to predict a likelihood that a subject is affected by a medical condition using an image division, in accordance with some of the disclosed embodiments.

FIG. 3 illustrates an exemplary process 300 that processor 110 may be configured to perform. For example, as discussed above, processor 110 may be configured to perform process 300 by executing software or firmware stored in memory device 120, or may be configured to perform process 300 using dedicated hardware or one or more ASICs.

Processor 110 may be configured to receive information reflective of an external soft tissue image of the subject (step 310). Processor 110 may be configured, for example, to perform step 310 in the same manner as step 210, discussed above.

Processor 110 may be configured to divide the external soft tissue image information into a plurality of regions (step 320). For example, processor 110 may be configured to process at least one of a forehead region of the external soft tissue image information, a periorbital region of the external soft tissue image information, a nasal region of the external soft tissue image information, a mid-face region of the external soft tissue image information, an ear region of the external soft tissue image information, and an oral region of the external soft tissue image information, and discount at least one other region of the external soft tissue image information. Particular regions in the external soft tissue image information may be defined in accordance with, for example, any of the techniques described above. For example, as depicted in FIG. 23B, a small grid may be applied to a nasal region of the external soft tissue image information. Areas surrounding the nasal region may be discounted by, for example, not having a small grid applied to them.

Figure 27:
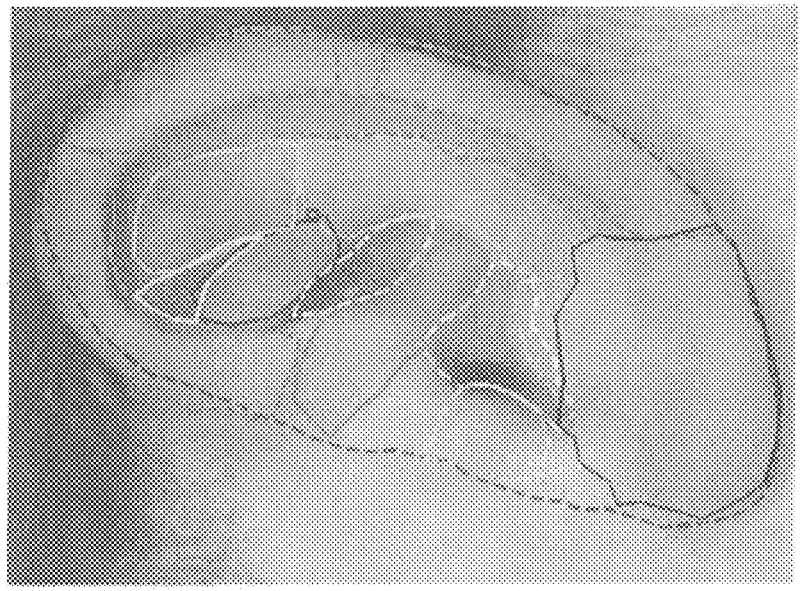
FIG. 27 illustrates exemplary depictions of an ear analysis in accordance with some of the disclosed embodiments.

In addition, while regions associated with a face of the subject are discussed, other regions may also be processed. For example, the external soft tissue image information may also, or alternatively, include a side view of the subject that includes an ear region. FIG. 27 depicts an example of an ear region that is further divided into a plurality of regions.

Processor 110 may be configured to generate an analysis of each of the plurality of regions (step 330). For example, within each region, at least one of an anchored cell analysis and a shifting patch analysis may be performed. The anchored cell analysis and shifting patch analysis may be performed in the manner described above with respect to step 220. As described above, processor 110 may be configured to calculate a descriptor for each of the plurality of regions. The descriptor may include, for example, at least one of a combined appearance vector if an anchored cell analysis is performed and a descriptor vector if a shifting patch analysis is performed.

As described above, processor 110 may be configured to compare the plurality of regions with data derived from images of individuals known to be affected by the medical condition. For example, as described above, processor 110 may be configured to compare the descriptor to previously produced descriptors from additional external soft tissue images of other individuals previously determined to be affected by the medical condition. Based on the comparison, for each region, one or more probability scores associated with one or more dysmorphic features and/or one or more medical conditions may be determined.

Processor 110 may further be configured to aggregate the analyses of the plurality of regions (step 340). For example, an analysis of a nasal region may result in a first set of probability scores regarding dysmorphic features and/or medical conditions associated with the nasal region and an analysis of an ear region may result in a second set of probability scores regarding dysmorphic features and/or medical conditions associated with the ear region. The probability scores may be produced using, for example, the techniques described above. In some embodiments, some of the probability scores may be aggregated by combining the probability scores. For example, a particular dysmorphic feature and/or medical condition may be associated with both the nasal region and the ear region. A probability score for the particular dysmorphic feature and/or medical condition determined from the nasal region and another probability score for the particular dysmorphic feature and/or medical condition determined from the ear region may be input into a classifier trained using, for example, positive and negative examples of the particular dysmorphic feature and/or medical condition, to generate a third probability score reflective of a probability score associated with the particular dysmorphic feature and/or medical condition. As a result of the aggregation, a single probability score, for example, may be determined for a set of dysmorphic features and/or medical conditions.

Processor 110 may further be configured to determine a likelihood that the subject is affected by the medical condition based on the aggregated analyses (step 350). For example, in the same or substantially the same manner as described above with respect to step 260, one or more classifiers may be trained to receive a set of scores for a plurality of dysmorphic features and/or medical conditions and output a score representative of the likelihood that the subject is affected by the medical condition.

In some embodiments, the medical condition may be a known medical condition. However, some medical conditions can have unknown genetic causes. Processor 110 may be configured to identify an underlying genetic variation likely to cause a medical condition. For example, a database, such as the database discussed above, may include a plurality of external soft tissue images of individuals associated with a medical condition caused by an unknown genetic variation. The database may also include a plurality of genetic variation information of individuals having a medical condition caused by an unknown genetic variation. Processor 110 may be further configured to determine whether a common dysmorphology exists at the location of at least some of the plurality of external soft tissue images. For example, processor 110 may be configured to analyze the plurality of external soft tissue images in the manner described above to determine one or more dysmorphic features. A common dysmorphology may exist if, for example, a dysmorphic feature exists at the same or substantially the same location in at least two images.

Processor 110 may be further configured to analyze the plurality of genetic variation information to identify at least one common genetic variation. A common genetic variation may include, for example, a determination that a gene associated with one image matches a gene associated with another image. Processor 110 may be further configured to compare the location of the plurality of external soft tissue images with the common genetic variation. For example, a determination may be made whether the genetic variation is known to affect a body part containing the common dysmorphology location in the images. Processor 110 may be further configured to associate, in the database, at least one common location in the plurality of external soft tissue images and at least one common genetic variation in the plurality of genetic variation information.

Figure 4:
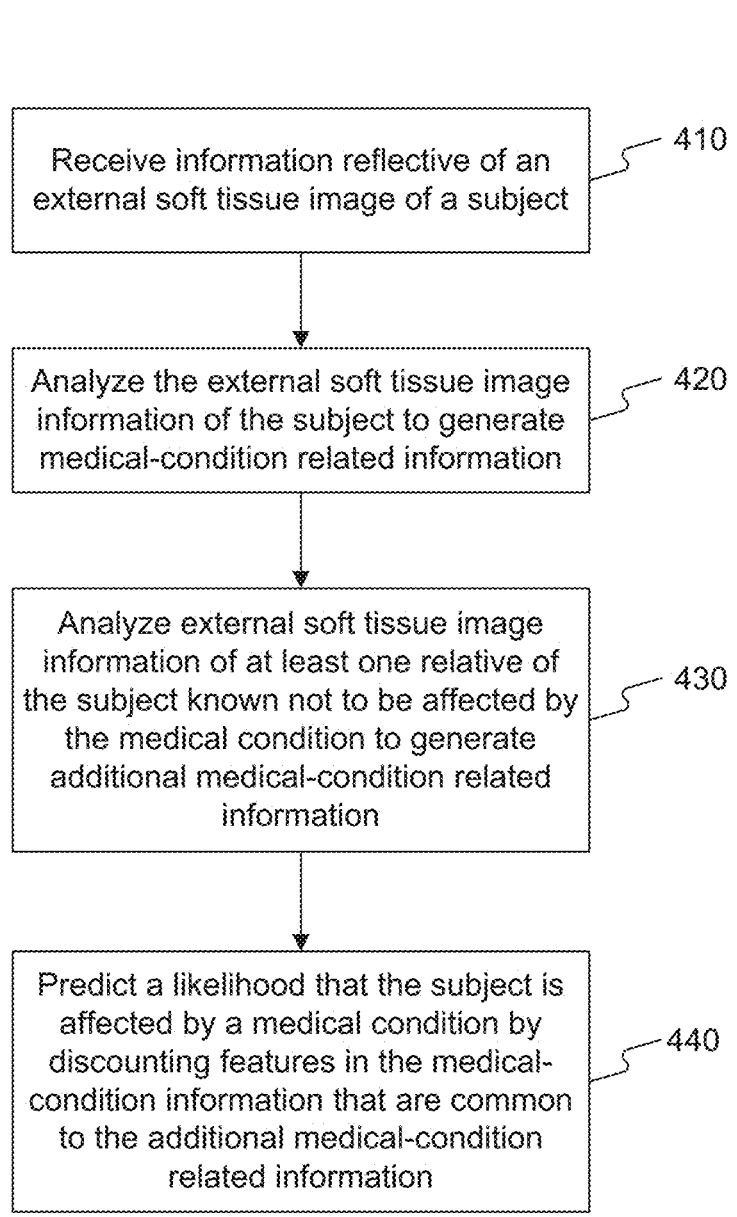
FIG. 4 illustrates example operations that a processor of a medical condition analysis system may be configured to perform to predict a likelihood that a subject is affected by a medical condition using information of at least one relative of the subject, in accordance with some of the disclosed embodiments.

FIG. 4 illustrates an exemplary process 400 that at least one processor may be configured to perform. For example, as discussed above, processor 110 may be configured to perform process 400 by executing software or firmware stored in memory device 120, or may be configured to perform process 400 using dedicated hardware or one or more ASICs.

Processor 110 may be configured to receive information reflective of an external soft tissue image of the subject (step 410). Step 410 may include substantially the same operations as step 210, discussed above.

Processor 110 may be further configured to analyze the external soft tissue image information of the subject to generate medical-condition related information (step 420). For example, medical-condition related information may be generated using the same or substantially the same operations described above with respect to steps 220-260. Optionally, however, only one analysis may be performed (e.g., the analysis in steps 220-230) rather than the two (or more) analyses described in steps 220-250. Medical-condition related information may include, for example, one or more scores for one or more dysmorphic features and/or one or more medical conditions.

Processor 110 may be further configured to analyze external soft tissue image information of at least one relative of the subject known not to be affected by the medical condition to generate additional medical-condition related information (step 430). For example, processor 110 may be configured to determine one or more scores associated with one or more dysmorphic features associated with the relative. Processor 110 may be configured to identify, for example, dysmorphic features having a high score that are usually indicative of a medical condition that the relative is known not to be affected by. In some embodiments, external soft tissue image information of a plurality of relatives is analyzed and dysmorphic features are identified having a high score for all of the relatives, or a number of relatives greater than a threshold, that are usually indicative of a medical condition that the relatives are known not to be affected by.

Additionally, or alternatively, processor 110 may be configured to determine one or more scores associated with one or more medical conditions associated with the relative. For example, processor 110 may initially utilize a classifier used for the general population to determine a score associated with a medical condition that the relative is known not to have. However, despite the relative not having the medical condition, processor 110 may determine a high score for the medical condition based on the analysis of the image information associated with the relative.

Processor 110 may be further configured to predict a likelihood that the subject is affected by a medical condition by discounting features in the medical-condition information that are common to the additional medical-condition related information (step 440). For example, as described above, processor 110 may determine one or more scores of one or more dysmorphic features from the image information of the subject. Based on the identified dysmorphic features of one or more relatives (e.g., the dysmorphic features of the relative that exhibit a high score usually indicative of a medical condition despite the relative being known not to be affected by the medical condition), processor 110 may be configured to modify or construct a classifier associated with a particular medical condition. For example, if a high score for a particular dysmorphic feature is usually used to increase the probability of a medical condition, but the relative has a high score for the particular dysmorphic feature and is known not to have the medical condition, the classifier may be modified or constructed such that the dysmorphic feature is ignored, is used to reduce the likelihood of the medical condition, or is used less heavily than for the general population in the determination of the likelihood of the medical condition. As another example, if processor 110 determines a high score for a medical condition for a relative of the subject despite the relative being known not to be affected by the medical condition, processor 110 may reduce any score determined for the medical condition for the subject. As another example, one or more images of the relative may be used to train the classifier. For example, one or more images of one or more relatives known not to be affected by a medical condition may be used a negative examples when training a classifier. As another example, only dysmorphic features of the subject that are different than one or more dysmorphic features of one or more relatives known not to be affected by a medical condition may be used in the likelihood determination.

Figure 5:
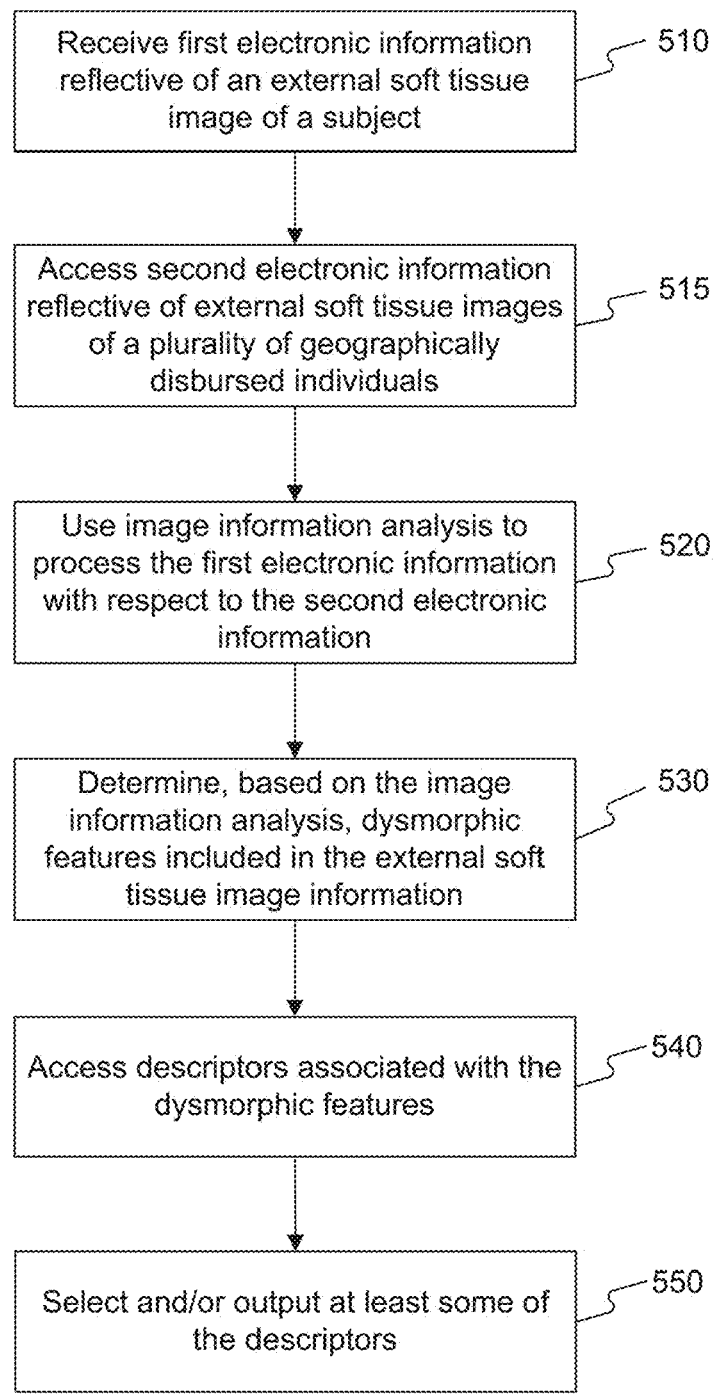
FIG. 5 illustrates example operations that a processor of a medical condition analysis system may be configured to perform to output at least some descriptors associated with dysmorphic features, in accordance with some of the disclosed embodiments.

FIG. 5 illustrates an exemplary process 500 that at least one processor may be configured to perform. For example, as discussed above, processor 110 may be configured to perform process 500 by executing software or firmware stored in memory device 120, or may be configured to perform process 500 using dedicated hardware or one or more ASICs.

Processor 110 may be configured to receive first electronic information reflective of an external soft tissue image of the subject (step 510). Processor 110 may be configured, for example, to perform step 510 in the same manner as step 210, discussed above. Further, the received information may be first electronic information reflective of first sets of values corresponding to pixels of a cranio-facial external soft tissue image of the subject. The first sets of values may correspond to relationships between at least one group of pixels in the cranio-facial soft tissue image of the subject. For example, the first sets of values may be pixel values corresponding to a region of interest in the cranio-facial external soft tissue image. The region of interest may be the entire cranio-facial external soft tissue image or a subset thereof, depending on implementation-specific considerations. For example, in some embodiments, only a predetermined section of the acquired cranio-facial external soft tissue image may be of interest because the predetermined section corresponds to a portion of the subject being screened for a symptom of a genetic condition. The relationship between the pixels in the at least one group of pixels may define, for instance, the spatial relationship between the pixels in the at least one group of pixels, the relative values of the pixels in the at least one group of pixels, or any other informative relationship.

Processor 110 may be configured to access second electronic information reflective of external soft tissue images of a plurality of geographically disbursed individuals (step 515). The second electronic information may be further reflective of second sets of values corresponding to pixels of cranio-facial external soft tissue images of the plurality of geographically dispersed individuals. The second sets of values may correspond to pixel values of associated pixels in digital images of the plurality of geographically dispersed individuals. As used herein, geographically dispersed individuals may be geographically dispersed, for example, in different countries, states, counties, cities, etc. Indeed, geographical dispersion encompasses individuals located in a variety of types of geographies, such as different physical locations, climates, elevations, etc.

Processor 110 may be configured to use image information analysis to process the first electronic information with respect to the second electronic information (step 520). For example, processor 110 may be configured to use image information analysis, wherein the image information analysis includes at least one of anchored cells analysis, shifting patches analysis, and relative measurements analysis. The anchored cell analysis, shifting patches analysis, and relative measurements analysis may be performed in the same or substantially the same manner as described above. As described above (for example, in step 220), processor 110 may analyze the external soft tissue image information based on a plurality of objective criteria, including at least one of age, gender, and ethnicity. For example, the only external soft tissue images in the database of other subjects of the same age, gender, and ethnicity as the subject may be utilized in the analysis.

Processor 110 may be further configured to determine, based on the image information analysis, dysmorphic features included in the external soft tissue image information (step 530). For example, as described above, one or more of an anchored cells analysis, shifting patches analysis, and relative measurements analysis may be used to assign a probability score to each dysmorphic feature in a set of dysmorphic features being analyzed.

Processor 110 may be further configured to access descriptors associated with the dysmorphic features, for example, from a suitable database of such descriptors (step 540). In some embodiments, the accessed descriptors include a list of words associated with dysmorphic features and that are potential indicators of at least one medical condition. For example, the accessed descriptors may include terms that are compatible with a plurality of databases, such as medical ontology databases, for searching medical conditions. The descriptors associated with the dysmorphic features may be obtained, for example, from a variety of sources including, for example, the International Statistical Classification of Diseases and Related Health Problems (e.g., ICD-9 or ICD-10), the Human Phenotype Ontology (HPO), and various other sources of descriptions for dysmorphic features, such as medical books, published journal papers, and computerized datasets. Processor 110 may be configured to link the descriptors associated with the dysmorphic features obtained from different sources (e.g., a descriptor for a particular dysmorphic feature used in ICD-10 may be linked to a descriptor for the particular dysmorphic feature used in HPO). Each descriptor for a dysmorphic feature may include, for example, a textugeal description and a list of synonyms. In some embodiments, HPO-based descriptors may be used as a reference list and all other lists from other sources may be mapped to it. If there is a term dysmorphic feature that is missing from HPO, it may be given a unique HPO-like numeric identifier and added to the reference list. In some embodiments, processor 110 may determine when HPO is updated and, based on a determined that HPO has updated, update the reference list. Moreover, in some embodiments, the accessed descriptors are a list of words that includes at least one description of a general appearance of a medical condition.

As one example, six high scoring dysmorphic features may be determined for image information of a subject. The descriptors for the dysmorphic features may include, for example, "Vermillion, Lower Lip, Thick", "Columella, High Insertion", "Hairline, High Anterior or Forehead, Tall", "Palpebral Fissure, Upslanted", "Eyebrow, Thick or Hypertrichosis of the Eyebrow or Bushy Eyebrow", "and "Philtrum, Tented." Thus, each of the descriptors may include, for example, a name of the dysmorphic feature (e.g., "Eyebrow, Thick") and possible alternatives to the dysmorphic feature (e.g., "Hypertrichosis of the Eyebrow").

Processor 110 may be further configured to select and/or output one or more of the descriptors (step 550). For example, processor 110 may be configured to output at least some of the descriptors to output device 150, for example, by reconfiguring the output device 150 to display a craniofacial image of the subject together with at least one descriptor and an indication in the image of the location of the at least one dysmorphic feature. Output device 150 may be, for example, a display. In some embodiments, as depicted in FIG. 1, output device 150 may be part of system 100. However, in other embodiments, output device 150 may be located remotely and processor 110 may be configured to send data to a device that includes output device 150 or is in communication with output device 150. A display may include, for example, one or more of a television set, computer monitor, head-mounted display, broadcast reference monitor, a liquid crystal display (LCD) screen, a light-emitting diode (LED) based display, an LED-backlit LCD display, a cathode ray tube (CRT) display, an electroluminescent (ELD) display, an electronic paper/ink display, a plasma display panel, an organic light-emitting diode (OLED) display, thin-film transistor display (TFT), High-Performance Addressing display (HPA), a surface-conduction electron-emitter display, a quantum dot display, an interferometric modulator display, a swept-volume display, a carbon nanotube display, a variforcal mirror display, an emissive volume display, a laser display, a holographic display, a light field display, a projector and surface upon which images are projected, a printer configured to generate a printout of data, or any other electronic device for outputting visual information.

Output device 150 may also be an audio device configured to output audio representative of, for example, at least some of the descriptors. The audio device may include, for example, a sound card and one or more speakers. Processor 110 may be configured, for example, to convert at least some of the descriptors into audio using a text-to-speech program.

In some embodiments, the descriptors may be presented in a list. In some embodiments, an image may be displayed near a descriptor that is indicative of the general location of the dysmorphic feature associated with the descriptor. For example, an image of an eye may be displayed next to a descriptor of "Eyebrow, Thick".

In some embodiments, a descriptor may be displayed at a location at, or close to, a dysmorphic feature to which it is associated. For example, the image information of the subject may be presented on the display. A descriptor (e.g., "Eyebrow, Thick") may be displayed on top of a region of the image information associated with a dysmorphic feature associated with the descriptor (e.g., "Eyebrow, Thick" may be displayed on top of an eye or eyebrow region of the image information).

Figure 6:
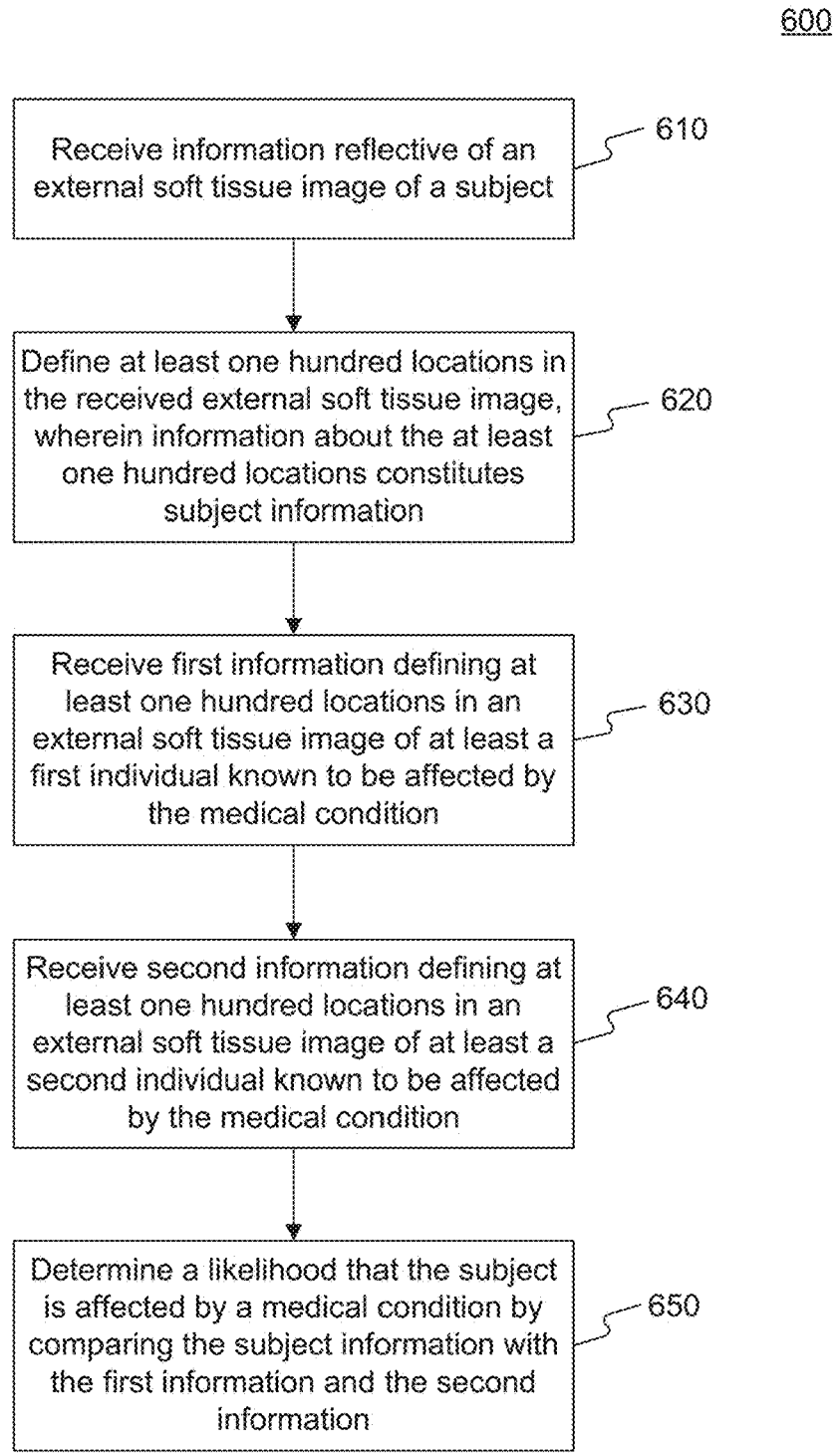
FIG. 6 illustrates example operations that a processor of a medical condition analysis system may be configured to perform to predict a likelihood that a subject is affected by a medical condition using at least one hundred defined locations on an image, in accordance with some of the disclosed embodiments.

FIG. 6 illustrates an exemplary process 600 that at least one processor may be configured to perform. For example, as discussed above, processor 110 may be configured to perform process 600 by executing software or firmware stored in memory device 120, or may be configured to perform process 600 using dedicated hardware or one or more ASICs.

Processor 110 may be configured to receive information reflective of an external soft tissue image of the subject (step 610). Processor 110 may be configured, for example, to perform step 610 in the same manner as step 210 discussed above.

Processor 110 may be configured to define at least one hundred locations in the received external soft tissue image information, wherein information about the at least one hundred locations constitutes subject information (step 620). Processor 110 may be configured to define the at least one hundred locations by determining at least one hundred feature points in the manner described above for determining feature points.

Processor 110 may also be configured to receive first information defining at least one hundred locations in at least an external soft tissue image of at least a first individual known to be affected by the medical condition (step 630) and to receive second information defining at least one hundred locations in at least an external soft tissue image of at least a second individual known to be affected by the medical condition (step 640). The subject information, the first information, and the second information may include, for example, vector data, ratio data, distance data, angular data, area data, and shape data associated with a relative measurements analysis calculated between at least some of the at least one hundred locations.

Processor 110 may be configured to determine a likelihood that the subject is affected by a medical condition by comparing the subject information with the first information and the second information (step 650). For example, processor 110 may be configured to determine a likelihood that the subject is affected by a medical condition by comparing the subject information with the first information and the second information using the relative measurements analysis described above.

In some embodiments, processor 110 may initially define a first number of feature points (e.g., one hundred feature points). The first number of feature points may permit processor 110 to determine the likelihood at a first speed. However, if the likelihood determination is inconclusive result (e.g., the likelihood is above a first threshold but below a second threshold), the above process may be repeated with a second number of feature points greater than the first number of feature points (e.g., one thousand feature points) that requires more time, but may be more accurate.

Figure 7:
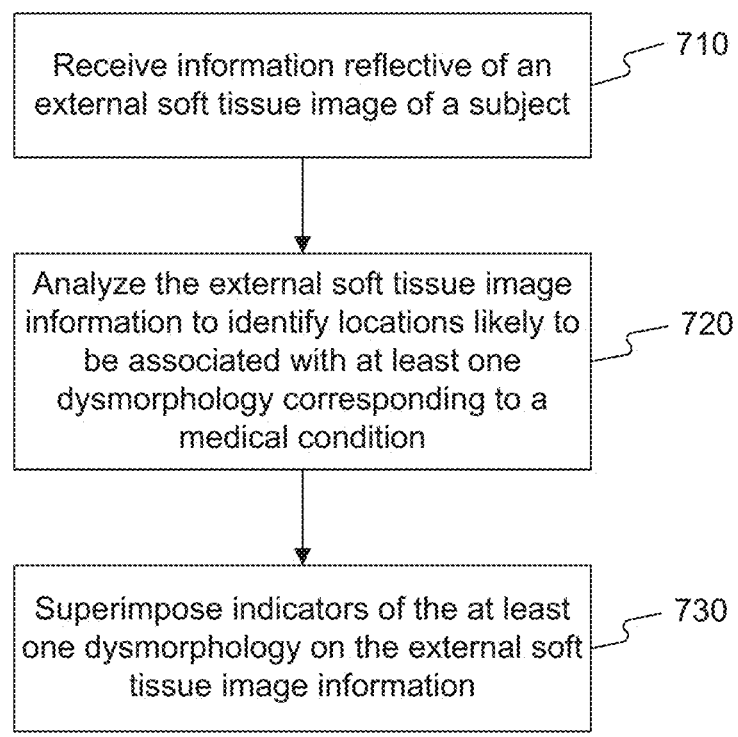
FIG. 7 illustrates example operations that a processor of a medical condition analysis system may be configured to perform to superimpose indicates of at least one dysmorphology on an image, in accordance with some of the disclosed embodiments.

FIG. 7 illustrates an exemplary process 700 that at least one processor may be configured to perform. For example, as discussed above, processor 110 may be configured to perform process 700 by executing software or firmware stored in memory device 120, or may be configured to perform process 700 using dedicated hardware or one or more ASICs.

Processor 110 may be configured to receive information reflective of an external soft tissue image of the subject (step 710). Processor 110 may be configured, for example, to perform step 710 in the same manner as step 210 discussed above.

Processor 110 may be configured to analyze the external soft tissue image information to identify locations likely to be associated with at least one dysmorphology corresponding to a medical condition (step 720). For example, processor 110 may be configured to identify one or more dysmorphic features having high probability scores in the manner described above.

Processor 110 may be configured to superimpose indicators of the at least one dysmorphology on the external soft tissue image information (step 730). For example, processor 110 may be configured to output to a display the external soft tissue image information along with a superimposed indication of at least one dysmorphology. For example, points detected in the image information may be superimposed on the image information. As another example, regions in the image information associated with high probability dysmorphic features may be highlighted. As another example, a heat map may be superimposed on the image information such that, at locations in the external soft tissue image information associated with a dysmorphic feature having a low score, a first translucent color may be used, whereas at locations in the external soft tissue image information associated with a dysmorphic feature having a high score, a second translucent color, different than the first translucent color, may be used. The locations may be chosen, for example, based on cells or patches used to determine the presence of the dysmorphic feature. In some embodiments, processor 110 may be configured to blur the heat map to produce a more appealing heat map.

Figure 8:
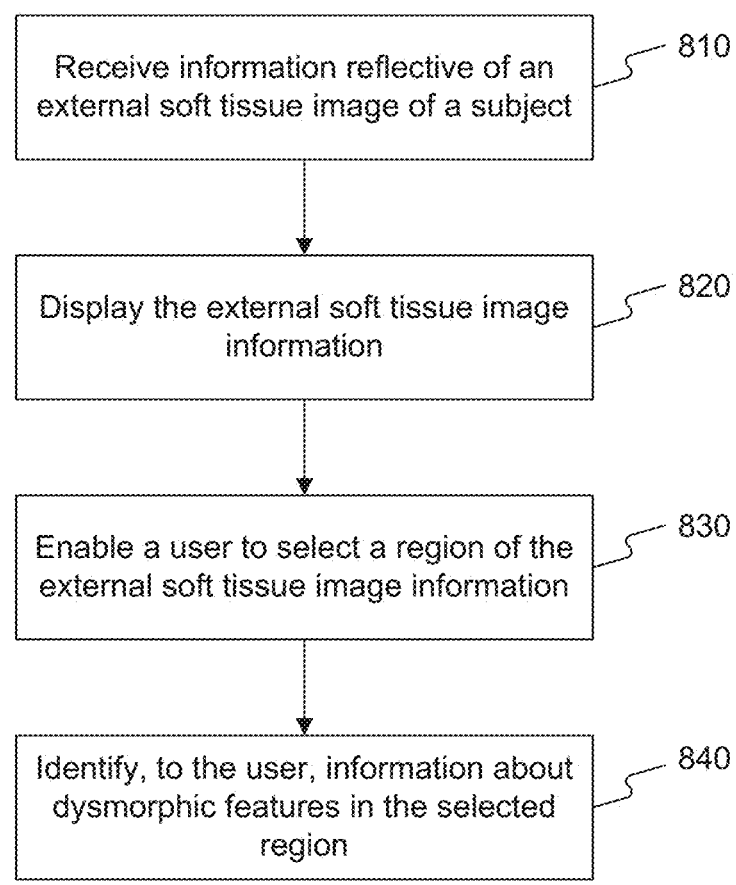
FIG. 8 illustrates example operations that a processor of a medical condition analysis system may be configured to perform to identify information about dysmorphic features in a selected region, in accordance with some of the disclosed embodiments.

FIG. 8 illustrates an exemplary process 800 that at least one processor may be configured to perform. For example, as discussed above, processor 110 may be configured to perform process 800 by executing software or firmware stored in memory device 120, or may be configured to perform process 800 using dedicated hardware or one or more ASICs.

Processor 110 may be configured to receive information reflective of an external soft tissue image of the subject (step 810). Processor 110 may be configured, for example, to perform step 810 in the same manner as step 210 discussed above.

Processor 110 may be configured to display the external soft tissue image information (step 820). For example, processor 110 may be configured to output the external soft tissue image information to a display that is configured in the manner described above.

Processor 110 may be configured to enable a user to select a region of the external soft tissue image information (step 830). For example, processor 110 may be configured to enable a user to select a region of the external soft tissue image information presented on the display. In some embodiments, the region selected by the user may be expanded after processor 110 detects the selection.

Processor 110 may be configured to identify, to the user, information about dysmorphic features in the selected region (step 840). For example, information about the dysmorphic features may be displayed in a list or may be superimposed onto the external soft tissue image information. The list of dysmorphic features may be presented, for example, in descending or ascending order of probability score.

Figure 9:
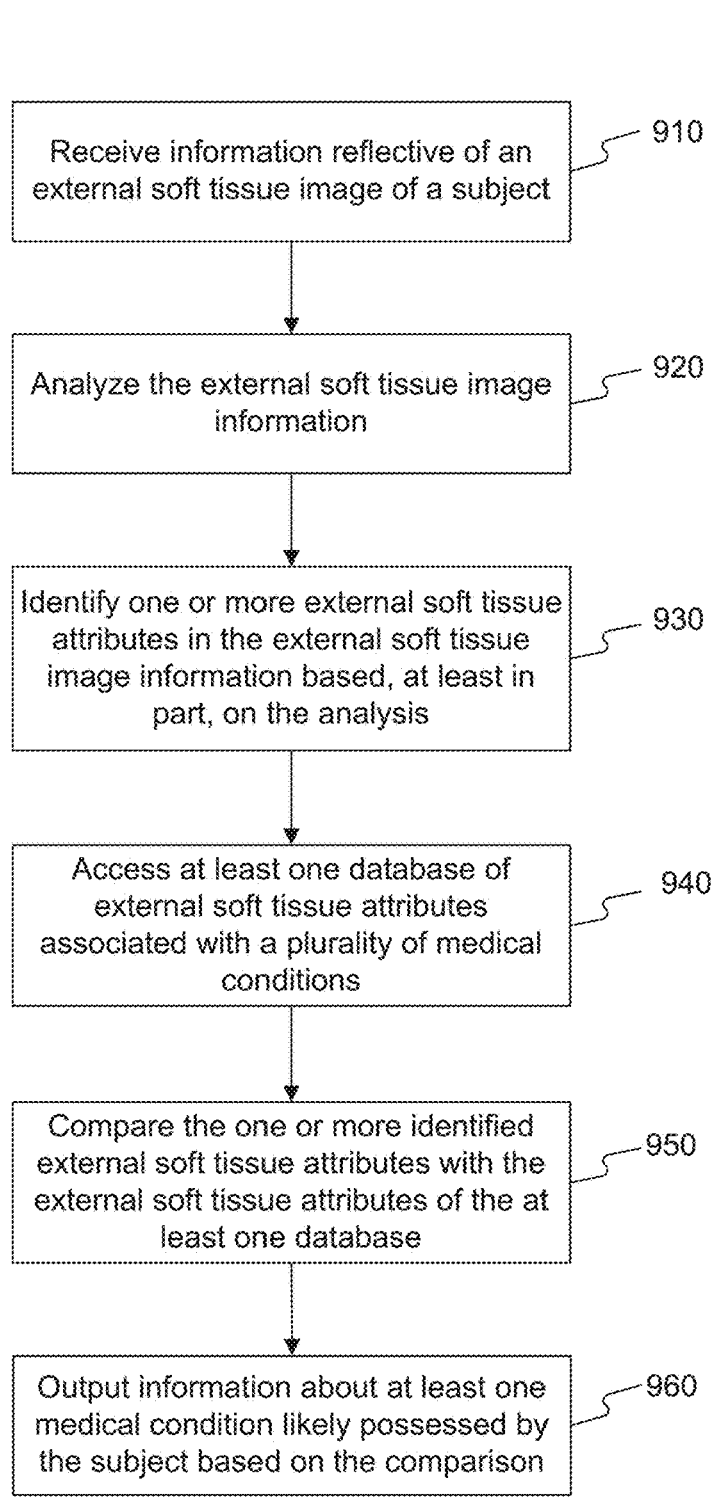
FIG. 9 illustrates example operations that a processor of a medical condition analysis system may be configured to perform to output information about at least one medical condition likely possessed by a subject, in accordance with some of the disclosed embodiments.

FIG. 9 illustrates an exemplary process 900 that at least one processor may be configured to perform. For example, as discussed above, processor 110 may be configured to perform process 900 by executing software or firmware stored in memory device 120, or may be configured to perform process 900 using dedicated hardware or one or more ASICs.

Processor 110 may be configured to receive information reflective of an external soft tissue image of the subject (step 910). Processor 110 may be configured, for example, to perform step 910 in the same manner as step 210 discussed above.

Processor 110 may be configured to analyze the external soft tissue image information (step 920). For example, processor 110 may analyze the external soft tissue image information using the same or substantially the same operations described above with respect to steps 220-260. Optionally, however, only one analysis may be performed (e.g., the analysis in steps 220-230) rather than the two (or more) analyses described in steps 220-250. For example, as described above, processor 110 may be configured to perform at least one of at least one of anchored cells analysis, a shifting patches analysis, and a relative measurements analysis.

Processor 110 may be configured to identify one or more external soft tissue attributes in the external soft tissue image information based, at least in part, on the analysis (step 930). The one or more external soft tissue attributes may include, for example, one or more dysmorphic features. For example, as described above, processor 110 may be configured to identify potential external soft tissue attributes in the external soft tissue image information and to assign a confidence level to the potential external soft tissue attributes reflective of a likelihood that the potential external soft tissue attributes appear in the image. In some embodiments, processor 110 may be configured to identify which external soft tissue attributes are indicators of medical conditions by taking into account a weighting of each external soft tissue attribute as an indicator of each medical condition. For example, processor 110 may identify all dysmorphic features having a high probability score or a probability score above a predetermined threshold. In some embodiments, the weighting of each external soft tissue attribute includes at least one of a severity of each external soft tissue attribute, a commonality of each external soft tissue attribute in a general population, and a relevance of each external soft tissue attribute to a medical condition.

Processor 110 may be configured to access at least one database of external soft tissue attributes associated with a plurality of medical conditions (step 940). For example, processor 110 may be configured to access a database containing data regarding one or more dysmorphic features and/or one or more medical conditions in the same manner as described above in, for example, step 220.

Processor 110 may be configured to compare the one or more identified external soft tissue attributes with the external soft tissue attributes of the at least one database (step 950). For example, processor 110 may be configured to compare the one or more identified external soft tissue attributes with the external soft tissue attributes of the at least one database in the same manner as described above in, for example, step 220. The comparison may generate one or more probability scores associated with one or more dysmorphic features.

Processor 110 may be configured to output information about at least one medical condition likely possessed by the subject based on the comparison (step 960). For example, as described above, processor 110 may be configured to input the one or more probability scores of the one or more dysmorphic features into a classifier to generate a probability score for a medical condition. In some embodiments, processor 110 is configured to determine additional information about the at least one medical condition likely possessed by the subject based directly on the analysis; and output the information about at least one medical condition likely possessed by the subject based on the comparison and the additional information. For example, as described in step 260, processor 110 may determine a likelihood of a medical condition based on both an initial medical condition likelihood and a set of dysmorphic feature probability scores.

Figure 10:
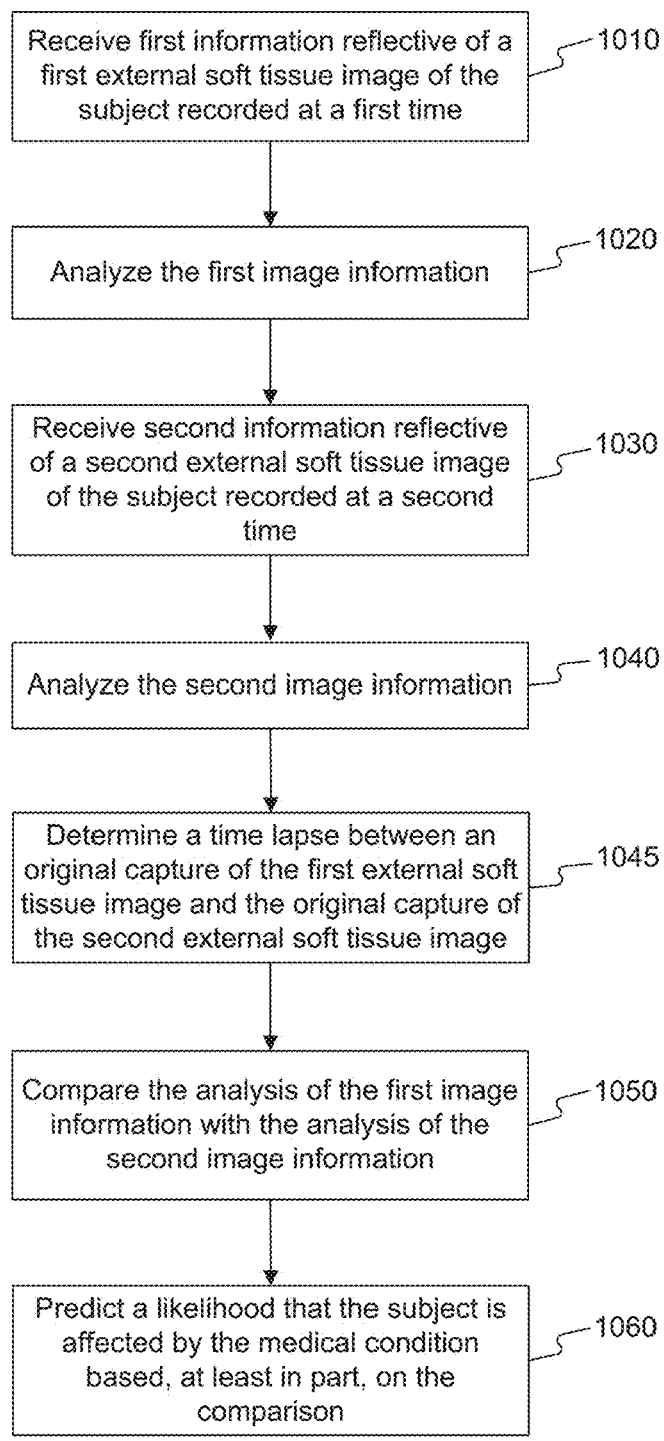
FIG. 10 illustrates example operations that a processor of a medical condition analysis system may be configured to perform to predict a likelihood that a subject is affected by a medical condition based on analyses at two different times, in accordance with some of the disclosed embodiments.

FIG. 10 illustrates an exemplary process 1000 that at least one processor may be configured to perform. For example, as discussed above, processor 110 may be configured to perform process 1000 by executing software or firmware stored in memory device 120, or may be configured to perform process 1000 using dedicated hardware or one or more ASICs.

Processor 110 may be configured to receive first pixel information being derived from a first external soft tissue image of the subject recorded at a first time (step 1010). Processor 110 may be configured, for example, to perform step 1010 in the same manner as step 210, discussed above. The first pixel information may be derived from a relationship between pixels in a first group of pixels in the first external soft tissue image. For example, the first group of pixels may correspond to a region of interest in the first external soft tissue image. The region of interest may be the entire first external soft tissue image or a subset thereof, depending on implementation-specific considerations. For example, in some embodiments, only a predetermined section of the acquired image may be of interest because the predetermined section corresponds to a portion of the subject being screened for a symptom of a genetic condition. The relationship between the pixels in the first group of pixels may define, for instance, the spatial relationship between the pixels in the first group of pixels, the relative values of the pixels in the first group, or any other informative relationship.

Processor 110 may be configured to analyze the first image information (step 1020), for example, by pre-analyzing a relationship (e.g., relative values) between the pixels in the first group of pixels. Processor 110 may be configured, for example, to analyze a relationship between the pixels in the first image information in the same manner as described above with respect to steps 220-260. Optionally, however, only one analysis may be performed (e.g., only the analysis in steps 220-230) rather than the two (or more) analyses described in steps 220-250. For example, in some embodiments the analysis includes at least one of anchored cells analysis, shifting patches analysis and relative measurements analysis. Moreover, as described above, in some embodiments the analysis includes a comparison of the first soft tissue image information to an external soft tissue image of at least one individual having at least one of substantially the same age, ethnicity, and gender as the subject.

Processor 110 may be configured to receive second information reflective of a second external soft tissue image of the subject recorded at a second time (step 1030). Processor 110 may be configured, for example, to perform step 1010 in the same manner as step 210 discussed above. The second pixel information may be derived from a relationship between pixels in a second group of pixels in the second external soft tissue image. For example, the second group of pixels may correspond to a region of interest in the second external soft tissue image. The region of interest may be the entire second external soft tissue image or a subset thereof, depending on implementation-specific considerations. For example, in some embodiments, only a predetermined section of the acquired image may be of interest because the predetermined section corresponds to a portion of the subject being screened for a symptom of a genetic condition. The relationship between the pixels in the second group of pixels may define, for instance, the spatial relationship between the pixels in the second group of pixels, the relative values of the pixels in the second group, or any other informative relationship.

The second time may be, for example, a predetermined amount of time after the first time or a non-scheduled time after the first time. In some embodiments, processor 110 may be configured to send an alert that second information reflective of a second external soft tissue image of the subject should be recorded. For example, if second information reflective of a second external soft tissue image of the subject has not been received within a predetermined amount of time, an alert may be sent to the subject's physician. As another example, if the analysis of the first information provided an indication that there is a low probability that a patient has a medical condition, an alert may be sent if second information reflective of a second external soft tissue image of the subject has not been received within a predetermined amount of time.

Processor 110 may be configured to analyze the second image information (step 1040), for example, by analyzing a relationship (e.g., relative values) between the pixels in the second group of pixels. Processor 110 may be configured, for example, to analyze the second image information in the same manner as described above with respect to steps 220-260. Optionally, however, only one analysis may be performed (e.g., the analysis in steps 220-230) rather than the two (or more) analyses described in steps 220-250. For example, in some embodiments the analysis includes at least one of anchored cells analysis, shifting patches analysis and relative measurements analysis. Moreover, as described above, in some embodiments the analysis includes a comparison of the second soft tissue image information to an external soft tissue image of at least one individual having at least one of substantially the same age, ethnicity, and gender as the subject.

In some embodiments, processor 110 is configured to apply the same technique to analyze the first external soft tissue image information and to analyze the second external soft tissue image information. For example, the technique applied at the first time may be recorded and reused the next time a subject is imaged. Alternatively, in some embodiments, if the analysis of the first image information did not indicate a likelihood of any medical condition, the analysis may be changed at the second time when the second external soft tissue image information is analyzed. As another alternative, if, for example, the analysis of the first image information indicated that there was a likelihood of a medical condition associated with a particular body part (e.g., an ear), the analysis of the second image information may be focused on the particular body part. In some embodiments, processor 110 may be configured to alert a party associated with capturing the second external soft tissue image to capture one or more images of the particular body part. The second external soft tissue image thus may include one or more images of the particular body part.

In certain embodiments, the first pixel information and/or the second pixel information may be received from a location corresponding to a storage location associated with the subject. For example, the first and/or second pixel information may be received from a cloud storage location associated with the subject, an electronic personal photo album of the subject, and so forth. Further, pixel information may be periodically received from one or more storage locations associated with the subject. For example, the processor 110 may be configured to monitor the pixel information associated with a subject over time by periodically receiving updated pixel information corresponding to updated external soft tissue images as the subject ages. This process may be automated such that the updated pixel information is automatically transferred to the processor from the one or more storage locations, or manual such that the subject or another designated agent manually initiates the transfers of the updated pixel information.

In some embodiments, the processor 110 may be configured to determine a time lapse between an original capture of the first external soft tissue image and an original capture of the second external soft tissue image (step 1045). The original capture of each of the respective images may correspond to the time at which each image was first acquired by an image acquisition device (e.g., a camera). For example, the original capture of the first external soft tissue image may occur when a camera is used to capture an image of the subject when the subject is twelve years old, and the original capture of the second external soft tissue image may occur when a camera is used to capture an image of the subject when the subject is fifteen years old. As such, the original capture of the image may correspond to the time when the image is initially captured by an image acquisition device, which may or may not correspond to when the processor 110 receives or accesses the images.

In some embodiments, the processor 110 may be configured to determine the time lapse based on metadata (e.g., geolocation data, timestamps, etc.) associated with one or both of the first external soft tissue image and the second external soft tissue image. For example, when the first and/or second soft tissue image is acquired by an image acquisition device (e.g., a camera), the image acquisition device may embed metadata into a file corresponding to the first and/or second soft tissue image. This embedded metadata may be accessed by the processor 110 to determined, for example, an acquisition date, acquisition time, acquisition location, etc. Further, in some embodiments, the processor 110 may be configured to account for one or more differences (e.g., different time zones) in the metadata associated with each of the first and second external soft tissue images.

Further, in certain embodiments, the processor 110 may determine the time lapse between the original capture of the first and second external soft tissue images by implementing an age detection algorithm configured to estimate the age of the subject in each of the images. For example, the age detection algorithm may be any algorithm, such as those known to those skilled in the art, capable of identifying the subject's age based on one or more factors in the image. The factors in the image may include any factors indicative of aging, for example, number of depth of wrinkles or lines, estimated skin firmness, or other changes in the subject's skin or features.

Processor 110 may be configured to compare, based on the determined time lapse, the analysis of the first image information (e.g., first pixel information) with the analysis of the second image information (e.g., second pixel information) (step 1050). For example, the first image information and the second image information may include probability scores for a number of dysmorphic features. Processor 110 may be configured to determine changes in probability scores of the dysmorphic features over time. The first image information and second image information may also include, for example, probability scores for a number of medical conditions. Processor 110 may be configured to determine changes in probability scores of the medical conditions over time.

As another example, the first image information and the second image information may also include one or more severity scores of one or more dysmorphic features. For example, the first image information and the second image information may include one or more severity scores based on one or more distances between feature points, angles formed by feature points, ratios between distances, ratios between angles, and the like. Thus, in some embodiments, processor 110 may be configured to monitor progress of the medical condition to determine a change in severity of an attribute over time.

Processor 110 may be configured to predict a likelihood that the subject is affected by the medical condition based, at least in part, on the comparison and/or the determined time lapse (step 1060). For example, in one embodiment, the processor 110 may be configured to predict, based on the time lapse, a likelihood that the subject is affected by the medical condition based. For further example, probability scores and severities of one or more dysmorphic features at the first time, probability scores and severities of one or more dysmorphic features at the second time, and/or changes in probability scores and severities of one or more dysmorphic features from the first time to the second time may be input into a classifier trained on, for example, positive and negative examples of a medical condition. If, for example, the severity or probability scores associated with a set of dysmorphic features increases from the first time to the second time, and the dysmorphic features are associated with a medical condition, a relatively high likelihood for the medical condition may be determined.

However, not all changes in severity will necessarily result in a high likelihood for the medical condition. For example, as a child ages, some the size of various dysmorphic features may be expected to change. Thus, in some embodiments, the change in severity of a dysmorphic feature may be compared to known changes that occur from the subject's age at the first time to the subject's age at the second time (optionally, known changes that occur from the subject's age at the first time to the subject's age at the second time may be examined in the context of at least one of the subject's gender, ethnicity, and any other category describing the subject). The known changes that occur from the subject's age at the first time to the subject's age at the second time may be determined, for example, by analyzing images in a database and determining norms for a given patient population. Thus, in some embodiments, if the change in severity of a dysmorphic feature deviates from an expected change, then a high likelihood that the subject is affected by the medical condition may be predicted. If the change in severity of a dysmorphic feature does not deviate from an expected change, then a low likelihood that the subject is affected by the medical condition may be predicted.

In some embodiments, processor 110 may increase a probability score determined at the second time if an increase in probability score from the first time to the second time is determined. In some embodiments, processor 110 may decrease a probability score determined at the second time if a decrease in probability score from the first time to the second time is determined.

Figure 11:
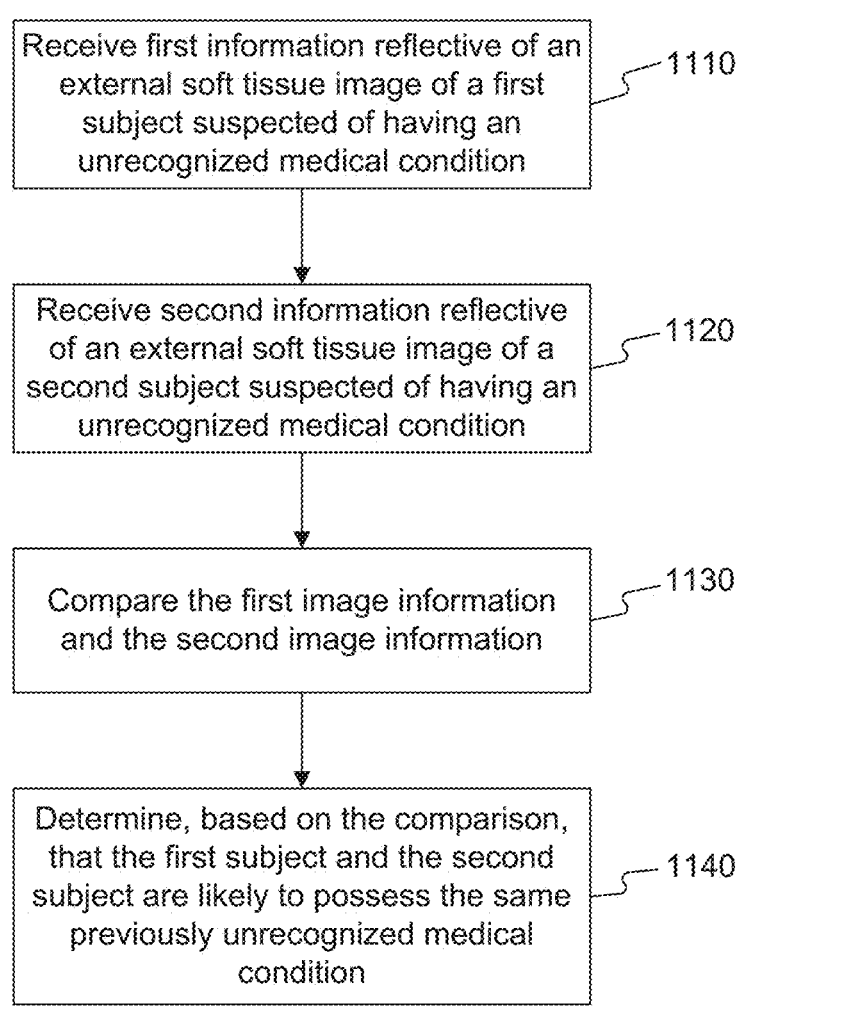
FIG. 11 illustrates example operations that a processor of a medical condition analysis system may be configured to perform to determine a previously unrecognized medical condition likely possessed by two subjects, in accordance with some of the disclosed embodiments.

In some embodiments, a plurality of additional sets of information may be received reflecting a plurality of additional external soft tissue images recorded at a plurality of additional times. Processor 110 may be configured to analyze the plurality of additional images, compare the analysis of the first soft tissue image information, the second soft tissue image information, and the additional sets of soft tissue image information, and predict the likelihood that the subject is affected by the medical condition based on the comparison of the analysis of the first soft tissue image information, the second soft tissue image information, and the additional sets of soft tissue image information FIG. 11 illustrates an exemplary process 1100 that at least one processor may be configured to perform. For example, as discussed above, processor 110 may be configured to perform process 1100 by executing software or firmware stored in memory device 120, or may be configured to perform process 1100 using dedicated hardware or one or more ASICs.

Processor 110 may be configured to receive first information reflective of an external soft tissue image of a first subject suspected of having an unrecognized medical condition (step 1110). Processor 110 may be configured, for example, to perform step 1110 in the same manner as step 210 discussed above.

Processor 110 may be configured to receive second information reflective of an external soft tissue image of a second subject suspected of having an unrecognized medical condition (step 1120). Processor 110 may be configured, for example, to perform step 1120 in the same manner as step 210 discussed above.

Figure 28:
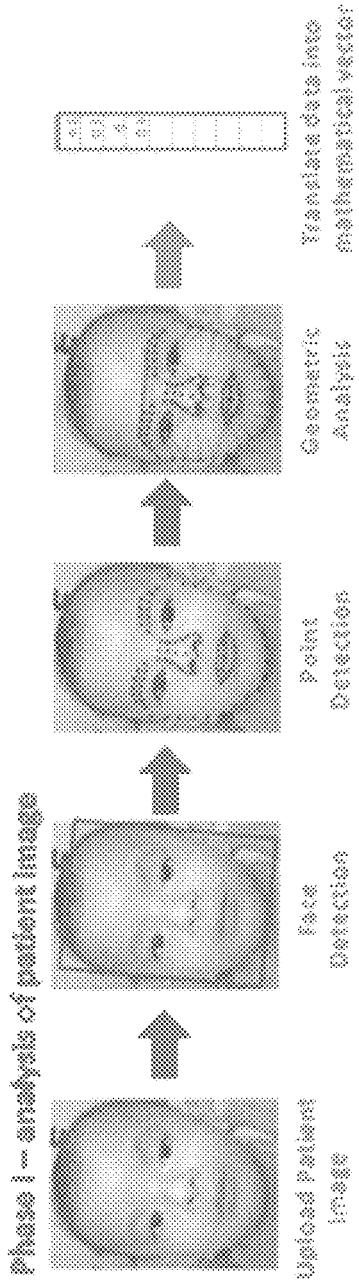
FIG. 28 illustrates exemplary depictions of an undiagnosed patient analysis in accordance with some of the disclosed embodiments.
Figure 28:
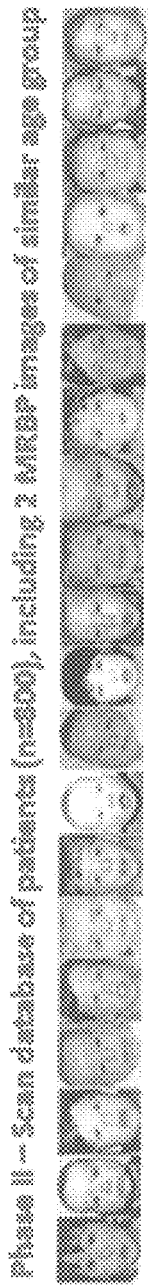
Figure 28:
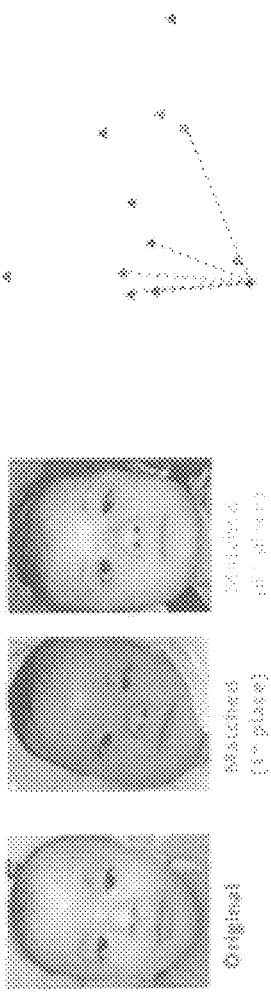

Processor 110 may be configured to compare the first image information and the second image information (step 1130). For example, a relative measurements analysis may be used to generate a vector of relative measurements for the first image information and the second image information. In some embodiments, the first image information is associated with a new subject and the second image information is associated with a previously presented individual. Thus, for example, as depicted in FIG. 28, a vector of relative measurements associated with the first image information may be compared against a set of vectors of relative measurements in a database (including the vector of relative measurements associated with the second image information). As another example, processor 110 may be configured to receive first image information from a first healthcare provider and receive the second image information from a second healthcare provider. Processor 110 may enable the first healthcare provider to access image information provided by the second healthcare provider but deny access to text data (e.g., a patient name) provided by the second healthcare provider, and vice versa.

Processor 110 may be configured to determine, based on the comparison, that the first subject and the second subject are likely to possess the same previously unrecognized medical condition (step 1140). For example, processor 110 may be configured to determine that the first subject and the second subject are likely to possess the same previously unrecognized medical condition if the first image information and the second image information have a high degree of similarity to each other and a high degree of dissimilarity to other images in the database. The similarity may be determined, for example, based on a comparison of the vectors of relative measurements (e.g., as graphically depicted in the bottom right of FIG. 28, a distance may be determined from a vector of relative measurements associated with the first image information to a vector of relative measurements associated with the second image information). Processor 110 may enable the first healthcare provider to communicate with the second healthcare provider if it is determined that the first subject and the second subject are likely to possess the same previously unrecognized medical condition.

Figure 12:
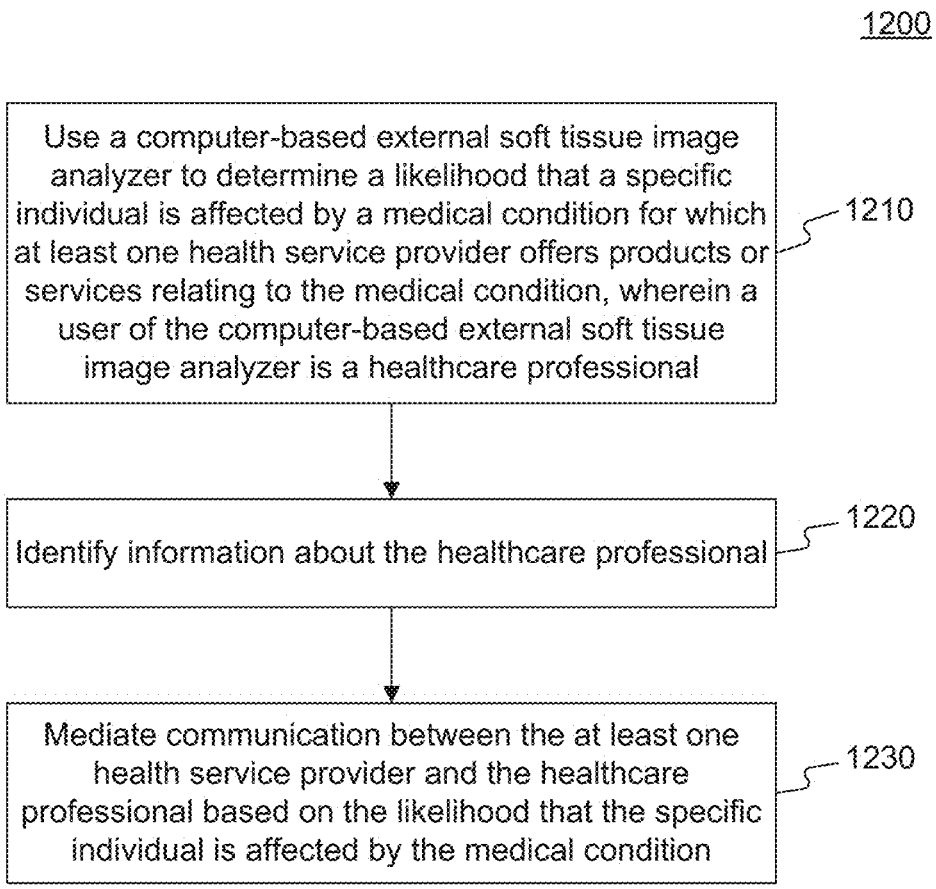
FIG. 12 illustrates example operations that a processor of a medical condition analysis system may be configured to perform to mediate communications between a health service provider and a healthcare professional, in accordance with some of the disclosed embodiments.

FIG. 12 illustrates an exemplary process 1200 that at least one processor may be configured to perform. For example, as discussed above, processor 110 may be configured to perform process 1200 by executing software or firmware stored in memory device 120, or may be configured to perform process 1200 using dedicated hardware or one or more ASICs.

Processor 110 may be configured to use a computer-based external soft tissue image analyzer to determine a likelihood that a specific individual is affected by a medical condition for which at least one health service provider offers products or services relating to the medical condition, wherein a user of the computer-based external soft tissue image analyzer is a healthcare professional (step 1210). For example, processor 110 may be configured to determine a likelihood that a specific individual is affected by a medical condition using the same operations as described above with respect to steps 210-260. Processor 110 may be configured to access a database that includes products or services offered by one or more health service providers and data associated the products or services with one or more related medical conditions. Thus, after determining a likelihood of a medical condition, processor 110 may determine whether at least one health service provider offers products or services relating to the medical condition.

Processor 110 may be configured to identify information about the healthcare professional (step 1220). For example, processor 110 may be configured to identify information including one or more of healthcare professional contact information, education, expertise, training, experience with the medical condition, and the like.

Processor 110 may be configured to mediate communication between the at least one health service provider and the healthcare professional based on the likelihood that the specific individual is affected by the medical condition (step 1230). For example, mediating may include alerting the healthcare professional of the existence of at least one of information regarding clinical trials, registries, diagnostics, and second opinions. An alert may be sent, for example, using a text message to a telephone number of the healthcare professional, using an email message to an email address of the healthcare professional, or using a telephone call to a telephone number of the healthcare professional. The alert may provide the healthcare professional with an option to contact (e.g., using text message, email, or telephone communication) the health service provider. In some embodiments, processor 110 may be configured to mediate if the likelihood is above a threshold. In some embodiments, processor 110 may be configured to mediate differently depending on the likelihood. For example, if the likelihood of the medical condition is moderate, then only the healthcare professional may receive a communication. If the likelihood of the medical condition is high, then both the health service provider and the healthcare professional may receive a communication.

Figure 13:
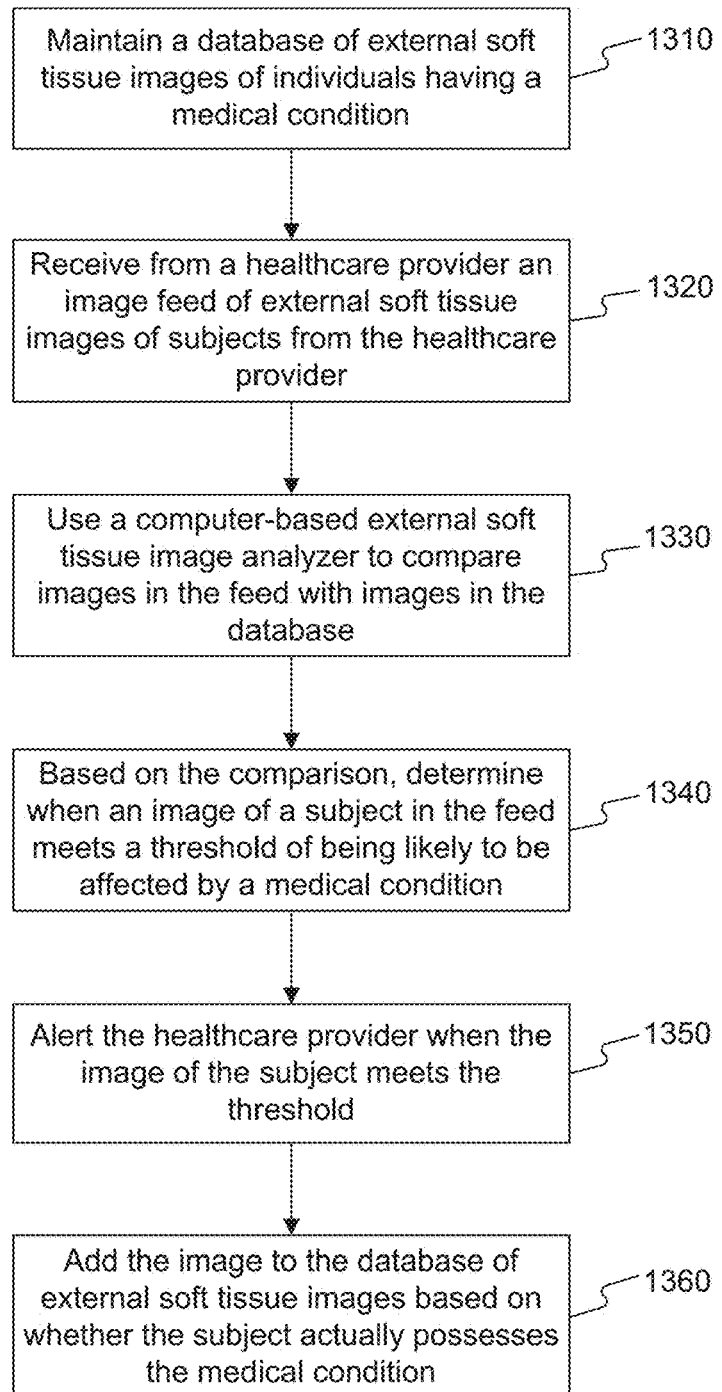
FIG. 13 illustrates example operations that a processor of a medical condition analysis system may be configured to perform to alert a healthcare provider when an image of a subject meets a threshold of being likely to be affected by a medical condition, in accordance with some of the disclosed embodiments.

FIG. 13 illustrates an exemplary process 1300 that at least one processor may be configured to perform. For example, as discussed above, processor 110 may be configured to perform process 1300 by executing software or firmware stored in memory device 120, or may be configured to perform process 1300 using dedicated hardware or one or more ASICs.

Processor 110 may be configured to maintain a database of external soft tissue images of individuals having a medical condition (step 1310). For example, processor 110 may be configured to maintain a database in accordance with any of the databases discussed above.

Processor 110 may be configured to receive from a healthcare provider an image feed of external soft tissue images of subjects from the healthcare provider (step 1320). For example, processor 110 may be configured receive each image in the image feed in accordance with the operations described above with respect to step 210. Moreover, processor 110 may be configured to receive one or more dysmorphic feature annotations associated with each received image. The dysmorphic feature annotations may be generated by, for example the healthcare provider or by any of the other techniques described herein. Moreover, processor 110 may be configured to receive one or more medical conditions associated with each received image. The medical condition may be generated by the healthcare provider or by any of the other techniques described herein.

Processor 110 may be configured to use a computer-based external soft tissue image analyzer to compare images in the feed with images in the database (step 1330). For example, processor 110 may be configured to compare each image in the feed with images in the database in accordance with the operations described above with respect to steps 220-250. Optionally, however, only one analysis may be performed (e.g., the analysis in steps 220-230) rather than the two (or more) analyses described in steps 220-250. In some embodiments, the annotated dysmorphic features and medical conditions may be used to limit the analysis. For example, in some embodiments, only a likelihood of the annotated dysmorphic features may be determined. Likewise, in some embodiments, only a likelihood of the medical conditions received with each image may be determined.

Processor 110 may be configured to, based on the comparison, determine when an image of a subject in the feed meets a threshold of being likely to be affected by a medical condition (step 1340). For example, processor 110 may be configured to determine when an image of a subject in the feed meets a threshold of being likely to be affected by a medical condition in accordance with the operations described above with respect to step 260.

Processor 110 may be configured to alert the healthcare provider when the image of the subject meets the threshold (step 1350). For example, processor 110 may be configured to send an alert to the healthcare provider using, for example, a text message, a telephone call, an email, and the like. As another example, processor 110 may be configured to present an alert on a display of the device that is used by the healthcare provider to capture the image. The alert may include, for example, a patient name or other patient identifier and data regarding the medical condition that triggered the alert. The data regarding the medical condition may include, for example, the name of the medical condition, dysmorphic features associated with the medical condition, suggested treatments for the medical condition, suggested additional tests for the medical condition, etc.

Processor 110 may be configured to add the image to the database of external soft tissue images based on whether the subject actually possesses the medical condition (step 1360). For example, processor 110 may be configured to receive confirmation from the healthcare provider that the subject possesses the medical condition. The confirmation may be based on, for example, the additional tests included in the alert.

In some embodiments, the images of the confirmed subjects and/or data derived from the confirmed subjects may be linked with the medical condition. For example, the database may be configured to annotate the confirmed subject data with the medical condition. The confirmed subject data may then be used to train one or more classifiers for the medical condition as a positive example of the medical condition. Likewise, processor 110 may also be configured to receive an indication from the healthcare provider that the subject does not possess the medical condition. The negative subject data may then be used to train one or more classifiers for the medical condition as a negative example (i.e., a control) or a false positive example.

Figure 14:
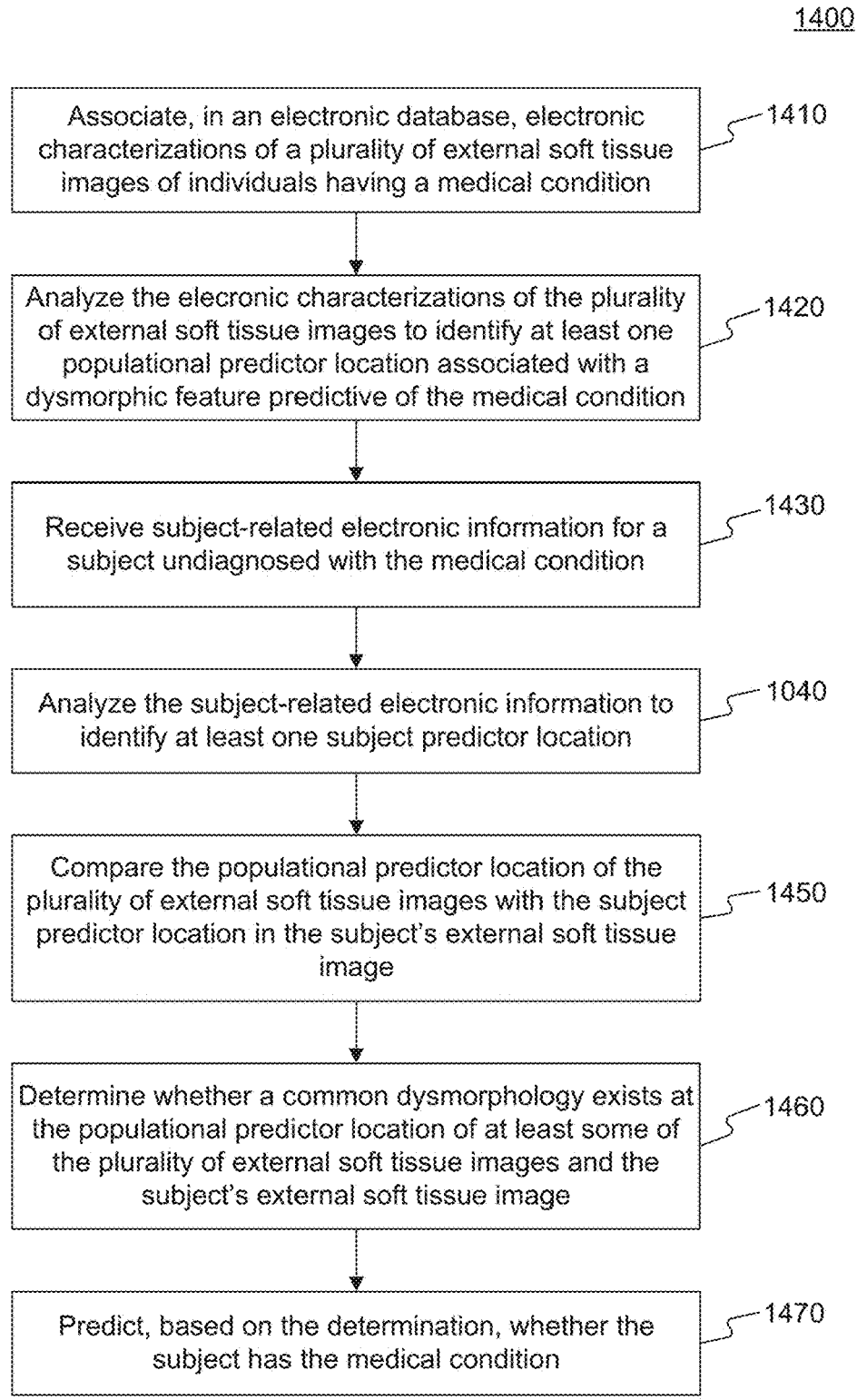
FIG. 14 illustrates example operations that a processor of a medical condition analysis system may be configured to perform to predict whether a subject has a medical condition, in accordance with some of the disclosed embodiments.

FIG. 14 illustrates an exemplary process 1400 that at least one processor may be configured to perform. For example, as discussed above, processor 110 may be configured to perform process 1400 by executing software or firmware stored in memory device 120, or may be configured to perform process 1400 using dedicated hardware or one or more ASICs.

In some embodiments, prior to implementing step 1410, the processor 110 may be configured to receive populational electronic information reflective of populational sets of values corresponding to pixels in a plurality of cranio-facial external soft tissue images associated with a plurality of geographically dispersed individuals having a medical condition, such as a genetic disorder. Each populational set of values may correspond to relationships between at least one group of pixels in each of the cranio-facial external soft tissue images. For example, each cranio-facial soft tissue image may be a digital image having an array of pixels, with each pixel having a populational value. The populational sets of values may be pixels values that are reflective of relationships between one or more groups of pixels in each of the cranio-facial external soft tissue images. For instance, in some applications, the at least one group of pixels may correspond to a region of interest in the cranio-facial external soft tissue images (e.g., one that corresponds to an anatomical location predicted to have an abnormality), and the populational sets of values may correspond to relationships between the pixels in the selected region of interest. As such, the populational sets of values may be actual pixel values corresponding to the pixels in the digital images, or some derivative thereof, which may, for example, be normalized across pixels in the at least one group of pixels (e.g., by setting the lowest pixel value to zero and adjusting the other pixel values accordingly).

Once the populational electronic information is received, the processor 110 may then use the populational sets of values to generate electronic characterizations of each of the plurality of cranio-facial external soft tissue images. The electronic characterizations may be any type of electronic representation of a subset or full set of the plurality of cranio-facial external soft tissue images. For example, in some embodiments, the electronic characterizations may be pixel values corresponding to a selected subset of the plurality of cranio-facial external soft tissue images and/or one or more selected portions of each of the plurality of cranio-facial external soft tissue images.

Processor 110 may be configured to associate, in an electronic database, the electronic characterizations of the plurality of external soft tissue images of individuals (e.g., geographically dispersed individuals) having a medical condition, such as one or more genetic disorders (step 1410). For example, processor 110 may be configured to associate a plurality of external soft tissue images of individuals having a medical condition in an electronic database in accordance with the operations described above.

Processor 110 may be configured to analyze the electronic characterizations of the plurality of external soft tissue images, and/or the plurality of external soft tissue images, which may be cranio-facial images, to identify at least one populational predictor location associated with an external soft tissue attribute (e.g., a dysmorphic feature) predictive of the medical condition, such as the one or more genetic disorders (step 1420). For example, processor 110 may be configured to detect one or more dysmorphic features using the operations described above. Processor 110 may be configured to determine whether a number of the external soft tissue images that are associated with individuals having a medical condition are also associated with one or more of the same dysmorphic features at, for example, a same or similar location.

Processor 110 may be configured to receive subject-related electronic information for a subject undiagnosed with the medical condition (step 1430). For example, processor 110 may be configured to receive an external soft tissue image of a subject in accordance with the same operations described with respect to step 210. In other embodiments, the subject-related electronic information may be reflective of subject-related sets of values corresponding to pixels of a cranio-facial external soft tissue image of the subject. The subject-related sets of values may correspond to relationships between at least one group of pixels in a cranio-facial external soft tissue image of the subject. For example, the cranio-facial external soft tissue image of the subject may be a digital image having an array of pixels, with each pixel having a subject-related value. The subject-related sets of values may be pixel values that are reflective of relationships between one or more groups of pixels in the cranio-facial external soft tissue image of the subject. For instance, in some applications, the at least one group of pixels may correspond to a region of interest in the cranio-facial external soft tissue image of the subject (e.g., one that corresponds to an anatomical location predicted to have an abnormality), and the subject-related sets of values may correspond to relationships between the pixels in the selected region of interest. As such, the subject-related sets of values may be actual pixel values corresponding to the pixels in the digital image, or some derivative thereof, which may, for example, be normalized across pixels in the at least one group of pixels (e.g., by setting the lowest pixel value to zero and adjusting the other pixel values accordingly).

Processor 110 may be configured to analyze the subject-related electronic information, and/or the subject's external soft tissue image to identify the subject predictor location corresponding to the populational predictor location (step 1440). For example, processor 110 may be configured to identify a region in the subject's external soft tissue image information corresponding to or containing the dysmorphic feature identified in step 1420.

Processor 110 may be configured to compare information associated with pixels corresponding to the populational predictor location of the plurality of external soft tissue images with information associated with pixels corresponding to the subject predictor location in the subject's external soft tissue image (step 1450) and to determine whether a common dysmorphology exists at the populational predictor location of at least some of the plurality of external soft tissue images and the subject predictor location of the subject's external soft tissue image (step 1460). For example, processor 110 may be configured to determine whether the region of the subject's external soft tissue image containing the predictor location is similar to one or more of the regions containing the predictor location in the plurality of external soft tissue images. For example, processor 110 may be configured to determine that one or more of the identified dysmorphic features are contained in the region of the subject's external soft tissue image containing the predictor location.

Processor 110 may be configured to predict, based on the determination, whether the subject has the medical condition, such as a genetic disorder (step 1470). For example, if one or more of the identified dysmorphic features are detected at the predicted location in the subject's external soft tissue image, then processor 110 may predict that the subject has the medical condition. Similarly, processor 110 may be configured to predict that the subject has the medical condition if a sufficient number of dysmorphic features are detected in a sufficient number of predictor locations.

Figure 15:
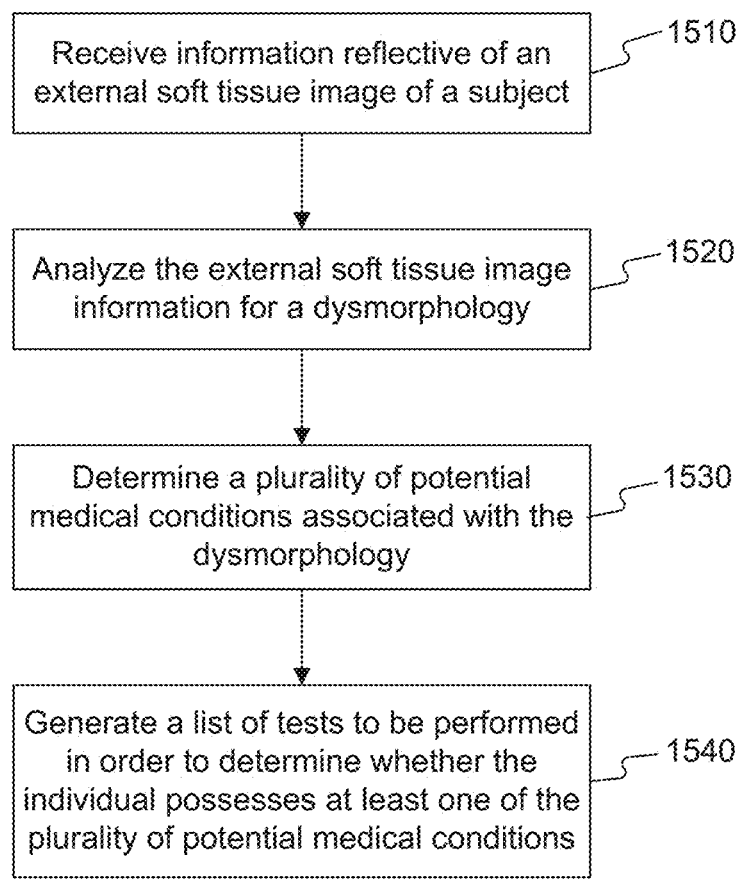
FIG. 15 illustrates example operations that a processor of a medical condition analysis system may be configured to perform to generate a list of tests to be performed, in accordance with some of the disclosed embodiments.

FIG. 15 illustrates an exemplary process 1500 that at least one processor may be configured to perform. For example, as discussed above, processor 110 may be configured to perform process 1500 by executing software or firmware stored in memory device 120, or may be configured to perform process 1500 using dedicated hardware or one or more ASICs.

Processor 110 may be configured to receive information reflective of an external soft tissue image of the subject (step 1510). Processor 110 may be configured, for example, to perform step 1510 in the same manner as step 210, discussed above.

Processor 110 may be configured to analyze the external soft tissue image information for a dysmorphology (step 1520). For example, processor 110 may be configured to analyze the external soft tissue image information using the same or substantially the same operations described above with respect to steps 220-250. Optionally, however, only one analysis may be performed (e.g., the analysis in steps 220-230) rather than the two (or more) analyses described in steps 220-250.

Processor 110 may be configured to determine a plurality of potential medical conditions associated with the dysmorphology (step 1530). For example, processor 110 may be configured to determine a plurality of potential medical conditions using the same operations described above with respect to step 260.

Processor 110 may be configured to generate a list of tests to be performed in order to determine whether the individual possesses at least one of the plurality of potential medical conditions (step 1540). For example, processor 110 may be configured to determine all tests having diagnostic value for a potential medical condition. In some embodiments, processor 110 may be configured to generate a list of tests based on at least one of the price of the test, the accuracy of the test, and the compatibility of the test with the plurality of potential medical condition.

In some embodiments, processor 110 may receive information reflective of previous tests that were selected in response to a generated list. Based on the received information, processor 110 may be configured to favor the selected tests. For example, if one test is more expensive than another test, processor 110 may be initially configured to output the cheaper test first. However, if processor 110 receives information indicating that the more expensive test is more widely used, then the more expensive test may be included first for subsequent generated lists.

Figure 16:
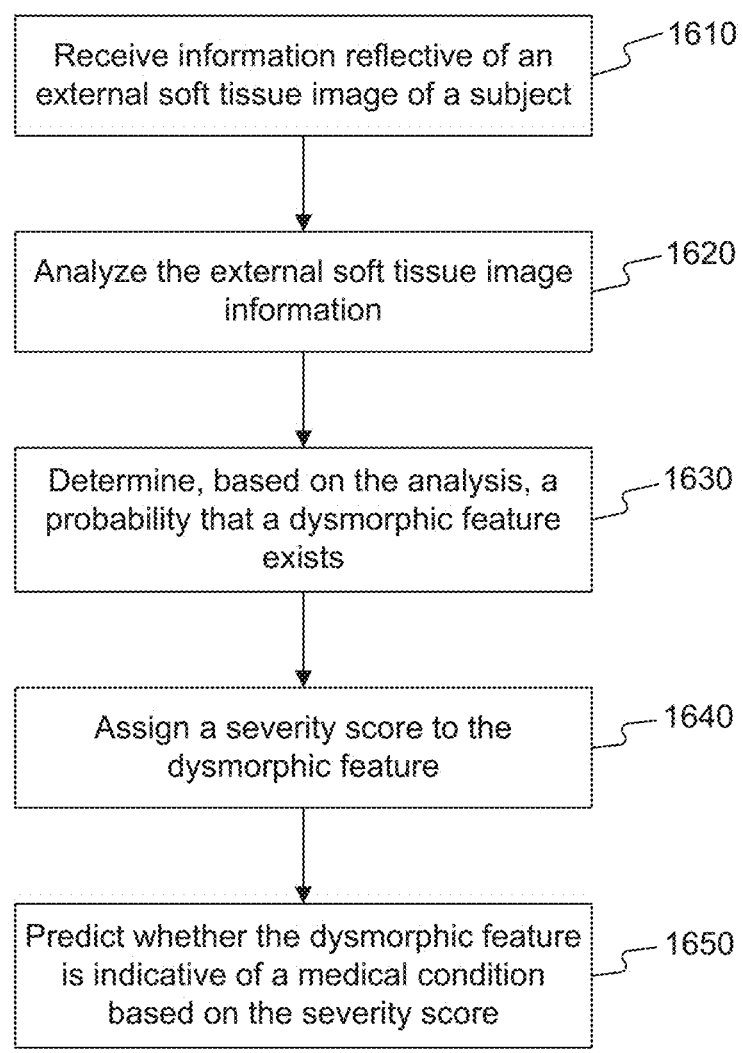
FIG. 16 illustrates example operations that a processor of a medical condition analysis system may be configured to perform to predict whether a dysmorphic feature is indicative of a medical condition based on a severity score, in accordance with some of the disclosed embodiments.

FIG. 16 illustrates an exemplary process 1600 that at least one processor may be configured to perform. For example, as discussed above, processor 110 may be configured to perform process 1600 by executing software or firmware stored in memory device 120, or may be configured to perform process 1600 using dedicated hardware or one or more ASICs.

Processor 110 may be configured to receive information reflective of an external soft tissue image of the subject (step 1610). Processor 110 may be configured, for example, to perform step 1610 in the same manner as step 210, discussed above.

Processor 110 may be configured to analyze the external soft tissue image information (step 1620). For example, processor 110 may be configured to analyze the external soft tissue image information using the same or substantially the same operations described above with respect to steps 220-250. Optionally, however, only one analysis may be performed (e.g., the analysis in steps 220-230) rather than the two (or more) analyses described in steps 220-250.

Processor 110 may be configured to determine, based on the analysis, a probability that a dysmorphic feature exists (step 1630). For example, processor 110 may be configured to determine a probability score of a dysmorphic feature using operations described above.

Processor 110 may be configured to assign a severity score to the dysmorphic feature (step 1640). For example, processor 110 may be configured to assign a severity score to a dysmorphic feature based on a relative measurements analysis. For example, the severity of a long philtrum dysmorphic feature may be measured by the ratio of the length defined by feature points associated with the philtrum to lengths defined by feature points associated with one or more of the nose, mouth, and height of a face of the subject. In some embodiments, the severity score is determined after a probability score is determined. For example, in some embodiments, if the probability score for a dysmorphic feature is above a threshold, the severity score may then be determined. The severity score may be determined as a function of a probability score for the dysmorphic feature (e.g., a higher probability score may receive a higher severity score) or by using a second classifier trained, for example, on data from individuals known to have various predetermined severities of the dysmorphic feature.

Processor 110 may be configured to predict whether the dysmorphic feature is indicative of a medical condition based on the severity score (step 1650). For example, a classifier may be trained on positive and negative examples of the medical condition to receive probability scores and severity scores associated with a set of dysmorphic features and to output a probability score for the medical condition. Processor 110 may, for example, use the trained classifier to determine whether the severity score of the dysmorphic feature is indicative of a medical condition.

Figure 17:
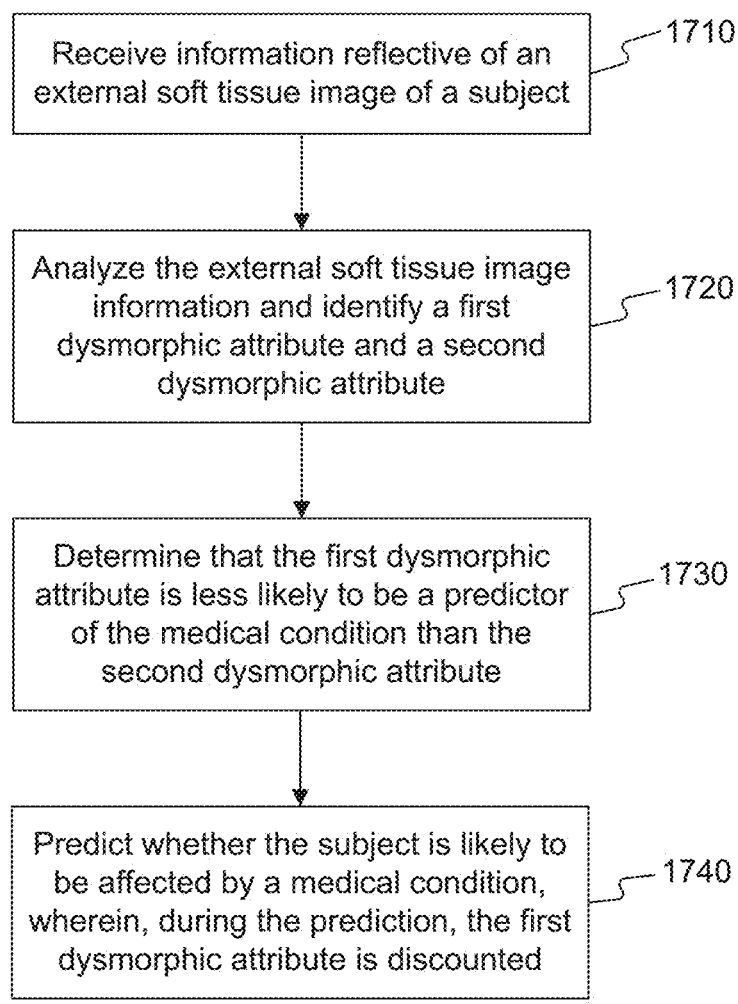
FIG. 17 illustrates example operations that a processor of a medical condition analysis system may be configured to perform to predict whether a subject is likely to be affected by a medical condition by discounting at least one dysmorphic feature, in accordance with some of the disclosed embodiments.

FIG. 17 illustrates an exemplary process 1700 that at least one processor may be configured to perform. For example, as discussed above, processor 110 may be configured to perform process 1700 by executing software or firmware stored in memory device 120, or may be configured to perform process 1700 using dedicated hardware or one or more ASICs.

Processor 110 may be configured to receive information reflective of an external soft tissue image of the subject (step 1710). Processor 110 may be configured, for example, to perform step 1710 in the same manner as step 210, discussed above.

Processor 110 may be configured to analyze the external soft tissue image information and identify a first dysmorphic attribute and a second dysmorphic attribute (step 1720). For example, processor 110 may be configured to analyze the external soft tissue image information and identify at least two dysmorphic features in the external soft tissue image information using the same or substantially the same operations described above with respect to steps 220-250. Optionally, however, only one analysis may be performed (e.g., the analysis in steps 220-230) rather than the two (or more) analyses described in steps 220-250.

Processor 110 may be configured to determine that the first dysmorphic attribute is less likely to be a predictor of the medical condition than the second dysmorphic attribute (step 1730). For example, processor 110 may be configured to determine that the first dysmorphic attribute is less likely to be a predictor of the medical condition than the second dysmorphic attribute based on information that the first dysmorphic attribute typically does not coincide with the second dysmorphic attribute. As another example, processor 110 may be configured to determine that the first dysmorphic attribute is less likely to be a predictor of the medical condition than the second dysmorphic attribute based on information that the first dysmorphic attribute is common amongst family members of the subject. As another example, processor 110 may be configured to determine that the first dysmorphic attribute is less likely to be a predictor of the medical condition than the second dysmorphic attribute based on information that the first dysmorphic attribute is common amongst members of the individual's ethnicity. As another example, processor 110 may be configured to determine that the first dysmorphic attribute is less likely to be a predictor of the medical condition than the second dysmorphic attribute based on information that the first dysmorphic attribute is common amongst members of the individual's gender.

Processor 110 may be configured to predict whether the subject is likely to be affected by a medical condition, wherein, during the prediction, the first dysmorphic attribute is discounted (step 1740). For example, processor 110 may be configured to predict whether the subject is likely to be affected by a medical condition using substantially the same operations described above with respect to step 260. However, the classifier used to make the prediction may, for example, be configured to ignore the first dysmorphic attribute or provide it with a reduced weight.

Figure 29:
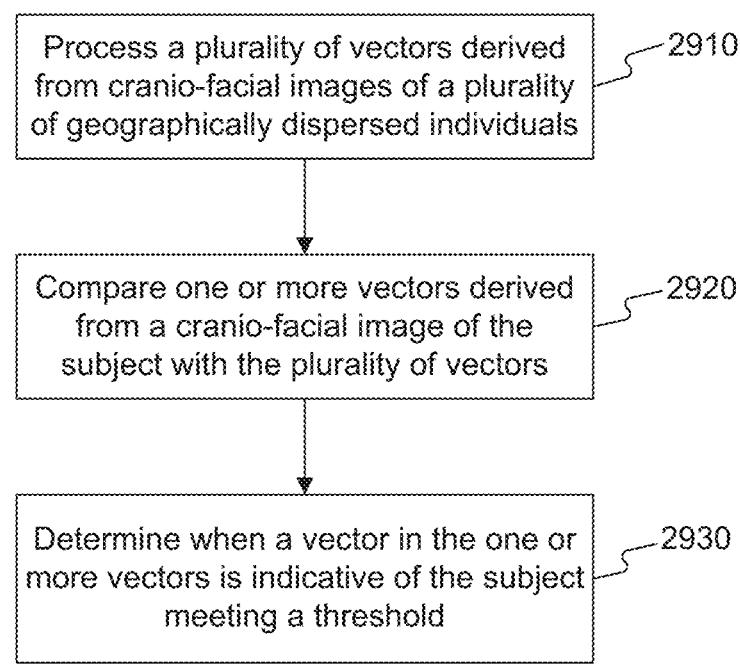
FIG. 29 illustrates exemplary depictions of a vector comparison analysis in accordance with some of the disclosed embodiments.

FIG. 29 illustrates an exemplary process 2900 that at least one processor may be configured to perform. For example, as discussed above, processor 110 may be configured to perform process 2900 by executing software or firmware stored in memory device 120, or may be configured to perform process 2900 using dedicated hardware or one or more ASICs.

Processor 110 may be configured to process a plurality of vectors derived from one or more images of geographically dispersed individuals having a medical condition (step 2910). For example, in one embodiment, the processor 110 may be configured to process a plurality of vectors derived from information extracted from cranio-facial images of geographically dispersed individuals having a genetic condition. More specifically, in some embodiments, the processor 110 may format and store the plurality of vectors in an electronic database for further use. In some embodiments, in the electronic database, the processor 110 may group vectors associated with like medical conditions (e.g., genetic disorders) together for future comparisons.

The vectors may be any type of image descriptors, for example, as described above with reference to the anchored cells analysis, shifting patches analysis, and relative measurements analysis. In additional to these image descriptors, extracted information from the image may include metadata, for example, corresponding to the age, gender, or other characteristics of the subject or image.

The processor 110 may be further configured to receive or access one or more vectors extracted from a cranio-facial image of a subject and to compare the one or more vectors to the plurality of vectors (step 2920). In some embodiments, the one or more vectors may be received from at least one healthcare provider of the subject. Healthcare providers may include, but are not limited to, one or more of physicians, geneticists, genetic counselors, medical researchers, dentists, pharmacists, physician assistants, nurses, advanced practice registered nurses, surgeons, surgeon's assistants, athletic trainers, surgical technologists, midwives, dietitians, therapists, psychologists, chiropractors, clinical officers, social workers, phlebotomists, occupational therapists, physical therapists, radiographers, respiratory therapists, audiologists, speech pathologists, optometrists, emergency medical technicians, paramedics, medical laboratory scientists, medical prosthetic technicians, and a wide variety of other human resources trained to provide some type of health care service, such as managers of health care services, clinical directors, lab directors, health information technicians, and other assistive personnel and support workers. Healthcare providers may include individuals working in hospitals, health care centers, laboratories, and other service delivery points, as well as in academic education, research groups, and administration and pharmaceutical companies.

In some embodiments, the processor 110 may implement a cranio-facial image or vector comparison of the one or more vectors with the plurality of vectors without reference to (i.e., without accessing, using, or visually comparing) the discernible cranio-facial image (e.g., the complete set of data encoding the acquired cranio-facial image) of the subject with the cranio-facial images of the geographically dispersed individuals. The foregoing feature may offer one or more advantages over systems that perform a cranio-facial image comparison between the images of the plurality of geographically dispersed individuals and the subject, respectively. For example, by making a comparison on the vector-level instead of the image-level, the privacy of the subject and/or the plurality of geographically dispersed individuals may be preserved.

The processor 110 may be further configured to determine when a vector in the one or more vectors is indicative of the subject meeting a threshold of being likely to be affected by a medical condition (step 2930). For example, the subject may be undiagnosed with a genetic condition, and the plurality of geographically dispersed individuals may be diagnosed with the genetic condition. As such, the threshold value may be a level of similarity between the vector in the one or more vectors and a vector in the plurality of vectors. In some embodiments, if the threshold level is met, the processor 110 may be further configured to alert a healthcare provider, for example, by displaying the alert on an output device. In still further embodiments, if the threshold level (or another predictive threshold level) is met the processor 110 may be configured to add the vector of the one or more vectors to the electronic database. For example, if the vector of the one or more vectors is similar enough to the plurality of vectors known to be associated with the genetic condition, there may be enough similarity to use the vector of the one or more vectors in future comparisons.

In some embodiments, the processor 110 may receive information from a healthcare provider regarding whether the subject has the genetic condition. If the subject does have the genetic condition, the processor 110 may add the vector of the one or more vectors to the electronic database. In other embodiments, the processor 110 may add the vector of the one or more vectors to the electronic database only if the subject is determined to have the genetic disorder, regardless of comparison to the threshold in step 2930.

Certain features which, for clarity, are described in this specification in the context of separate embodiments, may also be provided in combination in a single embodiment. Conversely, various features which, for brevity, are described in the context of a single embodiment, may also be provided in multiple embodiments separately or in any suitable sub-combination. Moreover, although features may be described above as acting in certain combinations and even initially claimed as such, one or more features from a claimed combination can in some cases be excised from the combination, and the claimed combination may be directed to a subcombination or variation of a subcombination.

Particular embodiments have been described. Other embodiments are within the scope of the following claims.

What is claimed is:

1. An electronic system for determining from a series of pixels in an image of external cranio-facial soft tissue whether a subject is likely to be affected by a medical condition, the system comprising:
   at least one memory for storing computer-executable instructions; and
   at least one processor configured to execute the stored instructions to:
   receive electronic information reflective of first values corresponding to pixels of an external soft tissue image of the subject, wherein the first values correspond to relationships between at least one group of pixels in the cranio-facial soft tissue image of the subject;
   analyze the first electronic information using at least one of an anchored cells analysis, a shifting patches analysis, and a relative measurements analysis;
   determine, based on the analysis, an indication that a dysmorphic feature exists;
   assign a severity score to the dysmorphic feature; and
   predict, based at least in part on the analysis, and based, at least in part, on the severity score, whether the dysmorphic feature is indicative of the medical condition.

2. The electronic system of claim 1, wherein the severity score corresponds to a probability that the dysmorphic feature exists.

3. The electronic system of claim 1, wherein the severity score corresponds to a magnitude of the dysmorphic feature relative to a specific population of individuals.

4. The electronic system of claim 1, wherein the dysmorphic feature is a first dysmorphic feature, and wherein the at least one processor is further configured to determine a probability that a second dysmorphic or non-dsymorphic feature exists and assign a second severity score to the second dysmorphic or non-dysmorphic feature.

5. The electronic system of claim 4, wherein the at least one processor is further configured to determine a likelihood that the subject possesses the medical condition based on the severity scores of the first dysmorphic feature and second dysmorphic or non-dysmorphic feature.

6. The electronic system of claim 1, wherein the at least one processor is further configured to output a list of a plurality of medical conditions associated with the dysmorphic feature.

7. The electronic system of claim 6, wherein the at least one processor is further configured to prioritize each of the plurality of medical conditions on the list based on the weighting of the severity score of the dysmorphic feature.

8. The electronic system of claim 1, wherein the at least one processor is further configured to assign the severity score accounting for a context of surrounding features on the external soft tissue image.

9. The electronic system of claim 1, wherein the indication is a probability.

10. A computer-implemented method for determining from a series of pixels in an image of external cranio-facial soft tissue whether a subject is likely to have a medical condition, the computer-implemented method comprising:
    receiving electronic information reflective of first values corresponding to pixels of an external soft tissue image of the subject, wherein the first values correspond to relationships between at least one group of pixels in the cranio-facial soft tissue image of the subject;
    analyzing the first electronic information using at least one of an anchored cells analysis, a shifting patches analysis, and a relative measurements analysis;
    determining, based on the analysis, an indication that a dysmorphic feature exists;
    assigning a severity score to the dysmorphic feature; and
    predicting, based at least in part on the analysis, and based, at least in part, on the severity score, whether the dysmorphic feature is indicative of the medical condition.

11. The computer-implemented method of claim 10, wherein the severity score corresponds to a probability that the dysmorphic feature exists.

12. The computer-implemented method of claim 10, wherein the severity score corresponds to a magnitude of the dysmorphic feature relative to a specific population of individuals.

13. The computer-implemented method of claim 10, wherein the dysmorphic feature is a first dysmorphic feature, and further comprising determining a probability that a second dysmorphic or non-dsymorphic feature exists and assigning a second severity score to the second dysmorphic or non-dysmorphic feature.

14. The computer-implemented method of claim 13, further comprising determining a likelihood that the subject possesses the medical condition based on the severity scores of the first dysmorphic features and the second dysmorphic or non-dysmorphic feature.

15. The computer-implemented method of claim 10, further comprising outputting a list of a plurality of medical conditions associated with the dysmorphic feature.

16. The computer-implemented method of claim 15, prioritizing each of the plurality of medical conditions on the list based on the weighting of the severity score of the dysmorphic feature.

17. The computer-implemented method of claim 10, wherein the assigning of the severity score includes accounting for a context of surrounding features on the external soft tissue image.

18. A non-transitory computer-readable medium for determining from a series of pixels in an image of external cranio-facial soft tissue whether a subject is likely to be affected by a medical condition, which comprises instructions that, when executed by at least one processor, cause the at least one processor to perform operations including:
    receiving electronic information reflective of first values corresponding to pixels of an external soft tissue image of the subject, wherein the first values correspond to relationships between at least one group of pixels in the cranio-facial soft tissue image of the subject;
    analyzing the first electronic information using at least one of an anchored cells analysis, a shifting patches analysis, and a relative measurements analysis;
    determining, based on the analysis, an indication that a dysmorphic feature exists;
    assigning a severity score to the dysmorphic feature; and
    predicting, based at least in part on the analysis, and based, at least in part, on the severity score, whether the dysmorphic feature is indicative of the medical condition.

19. A electronic system for determining from a series of pixels in an image of external cranio-facial soft tissue whether a subject is likely to be affected by a medical condition, the system comprising:
    at least one memory for storing computer-executable instructions; and at least one processor configured to execute the stored instructions to:

receive electronic information reflective of first values corresponding to pixels of an external soft tissue image of the subject, wherein the first values correspond to relationships between at least one group of pixels in the cranio-facial soft tissue image of the subject;

analyze the first electronic information using at least one of an anchored cells analysis, a shifting patches analysis, and a relative measurements analysis;

determine, based on the analysis, an indication that a dysmorphic feature exists;

predict, based at least in part on the analysis, whether the dysmorphic feature is indicative of the medical condition; and output a plurality of medical conditions associated with the dysmorphic feature.

20. The electronic system of claim 19, wherein the at least one processor is further configured to prioritize each of the plurality of medical conditions.

21. The electronic system of claim 20, wherein the at least one processor is configured to prioritize each of the plurality of medical conditions based on a weighting of a severity score assigned to the dysmorphic feature.

22. A computer-implemented method for determining from a series of pixels in an image of external cranio-facial soft tissue whether a subject is likely to have a medical condition, the computer-implemented method comprising:

receiving electronic information reflective of first values corresponding to pixels of an external soft tissue image of the subject, wherein the first values correspond to relationships between at least one group of pixels in the cranio-facial soft tissue image of the subject;

analyzing the first electronic information using at least one of an anchored cells analysis, a shifting patches analysis, and a relative measurements analysis;

determining, based on the analysis, an indication that a dysmorphic feature exists;

predicting, based at least in part on the analysis, whether the dysmorphic feature is indicative of the medical condition; and outputting a plurality of medical conditions associated with the dysmorphic feature.

23. The computer-implemented method of claim 22, further comprising prioritizing each of the plurality of medical conditions.

24. The computer-implemented method of claim 23, further comprising prioritizing each of the plurality of medical conditions based on a weighting of a severity score assigned to the dysmorphic feature.

\* \* \* \* \*